United States Patent
Kang et al.

(10) Patent No.: US 12,180,505 B2
(45) Date of Patent: Dec. 31, 2024

(54) NANOBARCODE FOR CONTROLLING CELL ADHESION AND DIFFERENTIATION OF STEM CELLS

(71) Applicant: Korea University Research and Business Foundation, Seoul (KR)

(72) Inventors: Heemin Kang, Seoul (KR); Young Keun Kim, Seoul (KR); Sunhong Min, Seoul (KR); Yoo Sang Jeon, Seoul (KR); Hyojun Choi, Seoul (KR)

(73) Assignee: KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 370 days.

(21) Appl. No.: 17/246,376

(22) Filed: Apr. 30, 2021

(65) Prior Publication Data
US 2021/0363488 A1 Nov. 25, 2021

(30) Foreign Application Priority Data
May 22, 2020 (KR) .......... 10-2020-0061704
Jun. 5, 2020 (KR) .......... 10-2020-0068518

(51) Int. Cl.
*C12N 5/0775* (2010.01)
*C07K 5/09* (2006.01)

(52) U.S. Cl.
CPC .......... *C12N 5/0662* (2013.01); *C07K 5/0817* (2013.01); *C12N 2501/998* (2013.01)

(58) Field of Classification Search
None
See application file for complete search history.

(56) References Cited

U.S. PATENT DOCUMENTS

2019/0008187 A1 1/2019 Konda et al.

FOREIGN PATENT DOCUMENTS

KR 10-2018-0039724 A 4/2018
KR 10-2034381 B1 10/2019

OTHER PUBLICATIONS

Sharma "Multi-segmented magnetic nanowires as multifunctional theranostic tools in nanomedicine" (2015) Univ. Minn., 1-257. (Year: 2015).*
Jeon et al. "Metallic Fe—Au Barcode Nanowires as a Simultaneous T Cell Capturing and Cytokine Sensing Platform for Immunoassay at the Single-Cell Level" (2019) Applied Mater & Interface, vol. 11: 23901-23908. (Year: 2019).*
Shore et al. "Enrichment and Quantification of Epitope-specific CD4+ T Lymphocyes using Ferromagnetic Iron-gold and Nickel Nanowires" (2018) Scientific Reports, vol. 8, article No. 15696. (Year: 2018).*
Anirudh Sharma et al., "Inducing cells to disperse nickel nanowires via integrin-mediated responses," Nanotechnology 2015 vol. 26, Mar. 12, 2015, 13 Pages.
Korean Office Action issued on Aug. 5, 2021, in connection with the corresponding Korean Patent Application No. 10-2020-0068518.

* cited by examiner

*Primary Examiner* — Teresa E Knight
(74) *Attorney, Agent, or Firm* — Hauptman Ham, LLP

(57) ABSTRACT

Disclosed are a nanobarcode for controlling adhesion and differentiation of stem cells and a method of controlling adhesion and differentiation of stem cells by using nanobarcodes. The method of controlling adhesion and differentiation of stem cells of the present invention may efficiently control adhesion and differentiation of stem cells in vivo or in vitro by tuning periodicity and sequences of a ligand peptide (RGD) of a nanobarcode.

7 Claims, 20 Drawing Sheets
(9 of 20 Drawing Sheet(s) Filed in Color)

NANOBARCODE FOR CONTROLLING CELL ADHESION AND DIFFERENTIATION OF STEM CELLS

CROSS REFERENCE TO RELATED APPLICATION

This present application is based upon and claims the benefit of priority to Korean Patent Application No. 10-2020-0061704 filed on May 22, 2020, and Korean Patent Application No. 10-2020-0068518 filed on Jun. 5, 2020 in the Korean Intellectual Property Office. The disclosures of the above-listed applications are hereby incorporated by reference herein in their entireties.

TECHNICAL FIELD

The present invention relates to a nanobarcode for controlling adhesion and differentiation of stem cells and a method of controlling adhesion and differentiation of stem cells by using the nanobarcode, and more particularly, to a method of controlling adhesion and differentiation of stem cells by using the nanobarcode.

BACKGROUND ART

Stem cells can proliferate through self-renewal, and have the potential to differentiate into various cells, such as bone, fat, muscle, myocardium, blood vessels, and cartilage. Recently, to regenerate damaged tissues and organs by using these characteristics, many studies have been conducted on transplantation of stem cells or cells differentiated from stem cells. In addition, biomaterials that can help stem cells to differentiate into specific cells are also being actively studied.

As a method of efficiently controlling the regenerative effect of stem cells, a technology through the presentation of ligand in vivo is used. However, there is a problem in that the existing micro-scale integrin ligand peptide (RGD) uncaging controls the adhesion of host stem cells but does not control the differentiation of stem cells.

PRIOR ART LITERATURE

Patent Document

Korean Patent Application Laid-Open No. 2018-0039724

SUMMARY OF THE INVENTION

To solve the aforementioned problems, the present invention provides a ligand-binding nanobarcode, and a method of controlling adhesion and differentiation of stem cells by tuning periodicity and sequences of ligands bound to the nanobarcode.

The present invention provides a nanobarcode for controlling adhesion and differentiation of stem cells, the nanobarcode including: a nanobarcode in which a first segment including iron (Fe) and a second segment including gold (Au) are repeatedly formed; and an integrin ligand peptide bound to the second segment of the nanobarcode.

Another exemplary embodiment of the present invention provides a method of preparing the nanobarcode for controlling adhesion and differentiation of stem cells, the method including: preparing a nanobarcode in which a first segment including iron (Fe) and a second segment including gold (Au) are repeatedly formed; substituting a carboxylate substituent on the first segment by mixing the nanobarcode and a first suspension; and mixing the nanobarcode and a second suspension including integrin ligand peptide (RGD).

Still another exemplary embodiment of the present invention provides a method of controlling adhesion and differentiation of stem cells, the method including: manufacturing a nanobarcode-presenting substrate by putting a substrate of which a surface is activated in a solution containing the nanobarcode for controlling adhesion and differentiation of the stem cells; and controlling adhesion and differentiation of stem cells after treating the nanobarcode-presenting substrate with stem cells.

The nanobarcodes for controlling adhesion and differentiation of stem cells according to the present invention facilitates adhesion and differentiation of stem cells by tuning periodicity and sequences of ligand coated to the nanobarcodes.

Further, the method of controlling adhesion and differentiation of stem cells according to the present invention may perform reversible control by applying a magnetic field to a substrate including the nanobarcodes, and efficiently control adhesion and differentiation of stem cells in vivo or in vitro.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Hereinafter, to describe the present invention more specifically, an exemplary embodiment of the present invention will be described in more detail with reference to the accompanying drawings. However, the present invention is not limited to the exemplary embodiment described herein, and may also be specified in other forms.

The present invention provides a nanobarcode for controlling adhesion and differentiation of stem cells including: a nanobarcode in which a first segment containing iron (Fe) and a second segment containing gold (Au) are repeatedly formed; and an integrin ligand peptide bound to the second segment of the nanobarcode.

Figure 1:
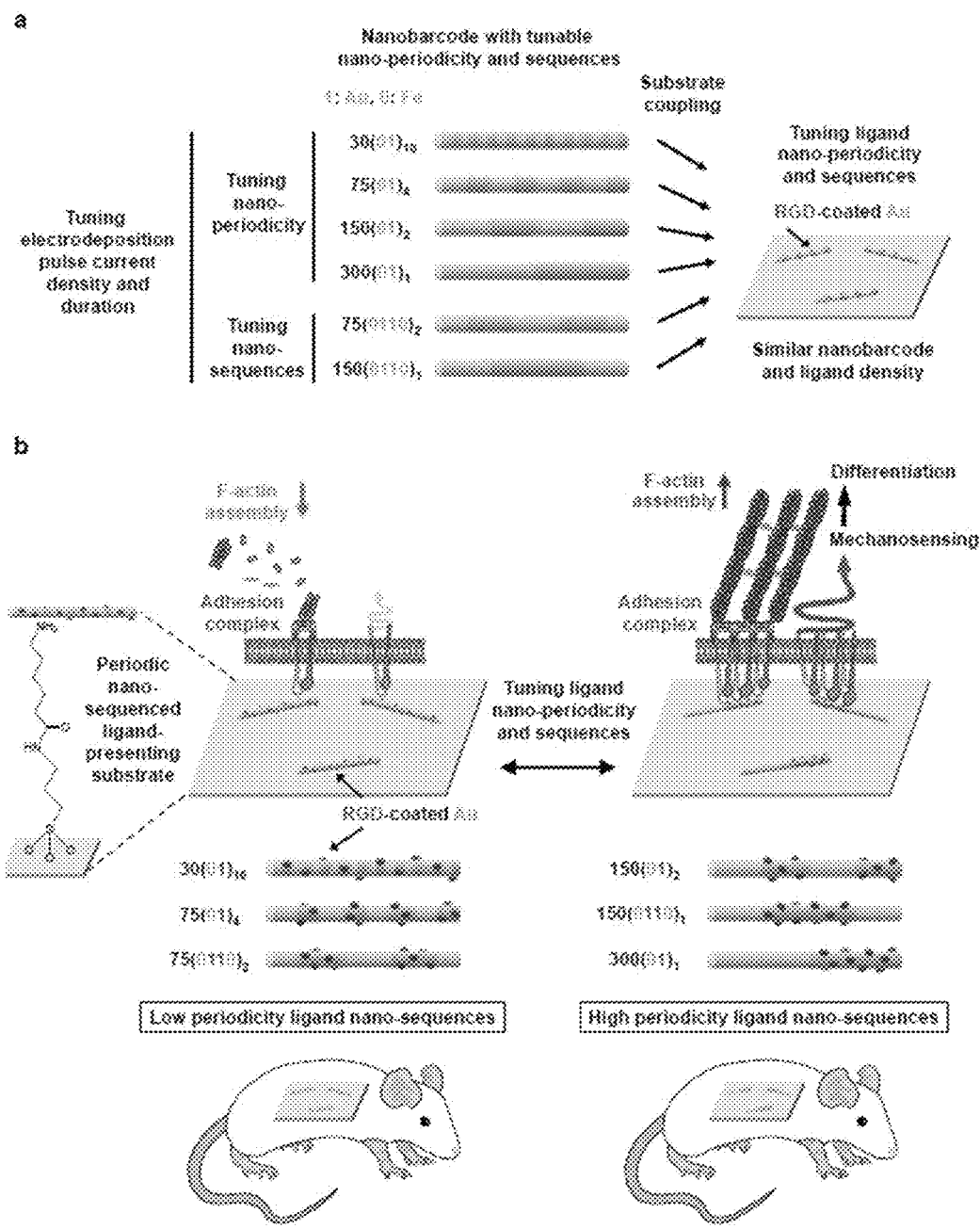
FIG. 1 is a schematic diagram illustrating a nanobarcode for controlling adhesion and differentiation of stem cells, a substrate including the same, and a method of controlling adhesion and differentiation of stem cells by using the same according to an exemplary embodiment of the present invention.

FIG. 1 is a schematic diagram illustrating a nanobarcode for controlling adhesion and differentiation of stem cells, a substrate coupled with the nanobarcode, and a method of controlling adhesion and differentiation of stem cells by using the same according to the present invention.

Referring to FIG. 1, it can be seen that the nanobarcode of the present invention includes a nanobarcode in which a first segment containing iron (Fe) and a second segment containing gold (Au) are repeatedly formed; and an integrin ligand peptide bound to the second segment of the nano barcode, in which the integrin ligand peptide is an integrin peptide.

In particular, the nanobarcode may be provided in a rod form satisfying Equation 1 or Equation 2.

$$[L(M_1 M_2)q] \qquad \text{[Equation 1]}$$

$$[L(M_1 M_2 M_2 M_1)q] \qquad \text{[Equation 2]}$$

Herein, $M_1$ is the first segment, $M_2$ is the second segment, q is the number of times of the repetition of the first and second segments, and L is the lengths of the first and second segments. In particular, L may be an integer between 10 and 500, 10 and 100, 30 and 75, or 150 and 500, $M_1$ and $M_2$ may represent independent numbers, and q may be an integer between 1 and 10, 2 and 10, or 1 and 2.

For example, in the nanobarcode, Equations 1 and 2 may be represented by any one of $[30(M_1M_2)_{10}]$, $[75(M_1M_2)_4]$, $[75(M_1M_2M_2M_1)_2]$, $[150(M_1M_2)_2]$, $[150(M_1M_2M_2M_1)_1]$, and $[300(M_1M_2)_1]$. In this case, $M_1$ means the first segment and $M_2$ means the second segment. In particular, the nanobarcode may be provided in a rod form satisfying any one of $[30(01)_{10}]$, $[75(01)_4]$, $[75(0110)_2]$, $[150(01)_2]$, $[150(0110)_1]$, and $[300(01)_1]$.

The nanobarcode satisfying Equation 1 may tune the periodicity of the ligand peptide bound to the second segment by controlling the lengths L of the first and second segments. The nanobarcode satisfying Equation 2 may tune any one or more of the periodicity and a sequence of the ligand peptide bound to the second segment compared to the nanobarcode satisfying Equation 1.

The first segment may be a structure in which a carboxylate is substituted. The carboxylate substituent may be an amino acid derivative, particularly aminocaproic acid. The first segment has the structure in which a carboxylate is substituted, thereby improving coupling force with the substrate and exhibiting excellent durability.

The integrin ligand peptide bound to the second segment may include a thiolated integrin ligand peptide, and may have a structure in which a thiol group of the integrin ligand peptide is chemically bound to the second segment. It is possible to efficiently control adhesion and differentiation of the stem cells by tuning the periodicity and sequences of the ligand peptide by binding the integrin ligand peptide to the second segment.

Figure 2:
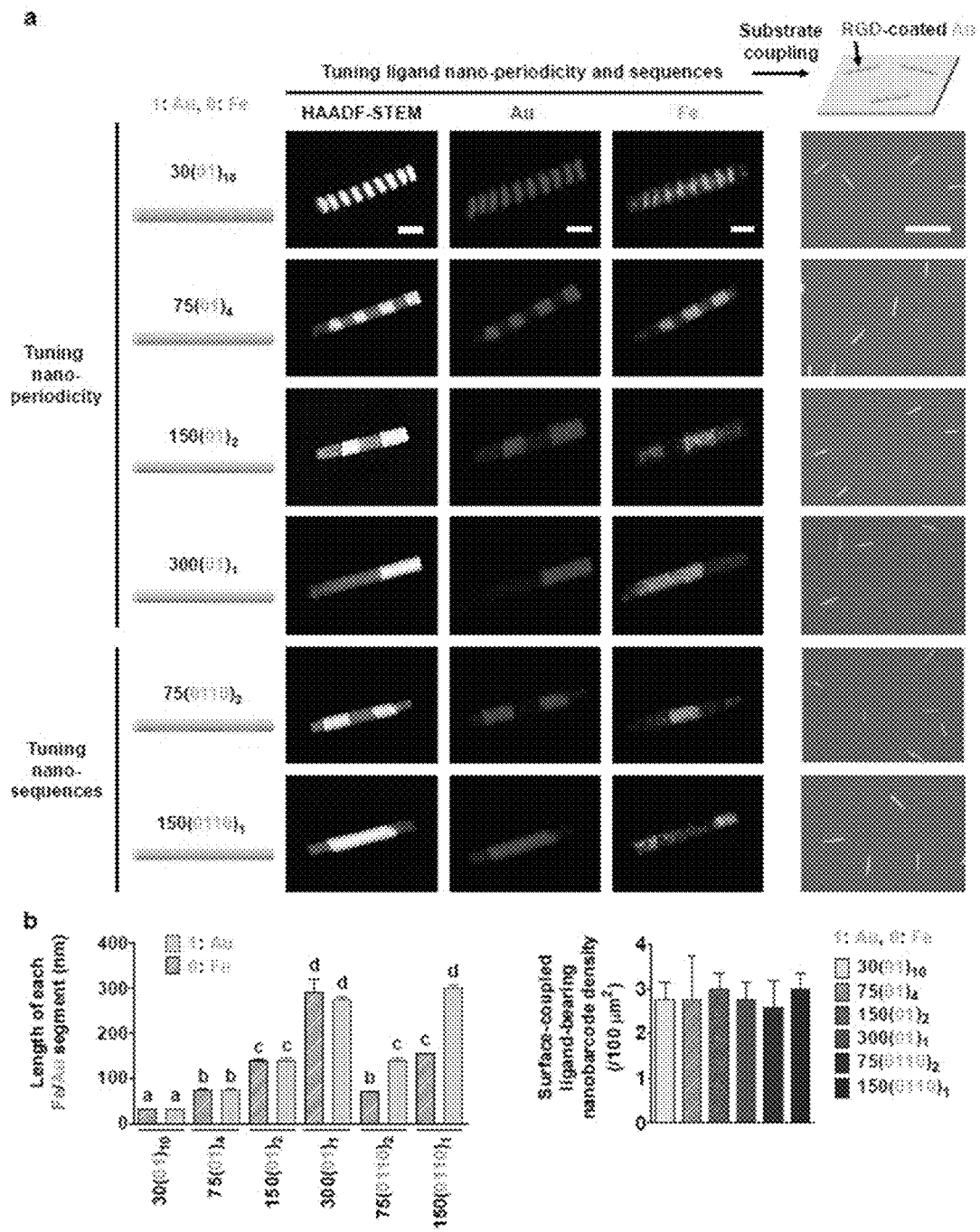
FIG. 2 is a High-angle annular dark field scanning transmission electron microscopy (HAADF-STEM) image, and energy dispersive spectroscopy (EDS) mapping and field emission scanning electron microscopy (FE-SEM) image of a nanobarcode according to the exemplary embodiment of the present invention.

Further, a of FIG. 2 is high-angle annular dark field scanning transmission electron microscopy images and field emission scanning electron microscopy images of the nanobarcode for controlling adhesion and differentiation of the stem cells according to the present invention, and it can show a size of the nanobarcode. In particular, the nanobarcode has a rod form with a circular cross section and may have a diameter of 50 nm to 100 nm. More particularly, the nanobarcode may have a diameter of 60 nm to 90 nm, or 50 nm to 80 nm. Further, the nanobarcode may have a rod form having a length of 200 nm to 1,000 nm. When the length of the nanobarcode is less than 200 nm, bonding efficiency of the integrin ligand may deteriorate, and when the length of the nanobarcode is larger than 1000 nm, the degree of distribution may deteriorate when nanobarcode is bound onto the substrate. More particularly, the nanobarcode may have a length of 500 nm to 800 nm, or 600 nm to 900 nm. The present invention includes the nanobarcode, thereby controlling the adhesion and differentiation of the stem cells according to the structure of the nanobarcode.

Further, the present invention provides a method of preparing the nanobarcode for controlling adhesion and differentiation of the stem cell, the method including: preparing a nanobarcode in which a first segment containing iron (Fe) and a segment containing gold (Au) are repeatedly formed; substituting a carboxylate substituent on the first segment by mixing the nanobarcode and a first suspension; and mixing the nanobarcode and a second suspension including the integrin ligand peptide (RGD).

The operation of preparing the nanobarcode may include an electroplating process and a process of etching an anodized nanotemplate in which iron and gold are alternately filled into pores of the nanotemplate by using a first current and a second current lower than the first current, respectively, by using the anodized nanotemplate to form an iron-gold multilayered nanowires.

As the nanotemplate, an anodic aluminum oxide (AAO) nanotemplate, an inorganic nanotemplate, or a polymer nanotemplate is used. Herein, the case which utilizes the AAO nanotemplate is illustrated. A diameter of the nanowire is determined according to a diameter of a pore of the AAO nanotemplate, and a length of the nanowire is determined according to a growth rate and duration time of each segment.

The used AAO nanotemplate includes the plurality of pores, of which a diameter has 200 nm.

A silver (Ag) electrode layer having a thickness of 250 nm is formed on the bottom surface of the AAO nanotemplate by an electron beam evaporation method before electroplating. The electrode layer serves as a cathode during electroplating. Herein, as the electrode layer, other metals or other conductive material layers may be used.

Fe/Au barcode nanowires are synthesized inside the AAO nanotemplate pores by a pulse plating method in which a voltage or a current is alternately applied so that an Fe layer is synthesized at a high voltage or current and an Au layer is synthesized at a low voltage or current.

A precursor solution for electroplating is prepared in which iron (II) sulfate heptahydrate ($FeSO_4$ $7H_2O$ 278.02 g/mol) and potassium dicyanoaurate(I) ($KAu(CN)_2$ 288.10 g/mol) are adjusted to have a certain ratio of mole concentration, in one plating bath. To maintain stable and mild environment during electroplating, boric acid ($H_3BO_3$) is added as a buffer solution.

Herein, since it is necessary to put two kinds of precursors into one plating bath and synthesize a nanowire containing two different elements, two kinds of precursors should not react and form a product when the precursors are selected.

Further, each element needs to be separated in the multilayer structure through modulating a ratio of the ionic content of the element with higher reduction potential to the content of the element with lower reduction potential. The ratio of the molar concentration of iron to gold ions in the used solution ranges 40:1 to 4:1 (preferably, 16:1), and the nanowire in which two kinds of elements form each layer respectively may be synthesized by adding a relatively low concentration of gold that is a noble metal.

The electrolyte is prepared by using deionized water, and the hydrogen ionization concentration (pH value) is kept constant by using boric acid ($H_3BO_3$) to maintain the stable and mild environment during electroplating.

The Fe/Au multilayer structure barcode-type nanowire is formed by performing pulse electroplating on the nanotemplate. The current of 10 mA/$cm^2$ was applied for electroplating the iron irons and the current of 1.0 mA/$cm^2$ was applied for electroplating the gold irons.

The iron and the gold have different standard reduction potentials, and by using the difference in the reduction potential, iron may be plated at a relatively high current, and gold may be plated at a relatively low current as described above. Therefore, it is possible to manufacture an Fe/Au multilayer thin film nanowire.

Next, to obtain an individual multilayer thin film nanowire, when the anodized nanotemplate is treated with a 1M sodium hydroxide (NaOH) solution at a room temperature for one hour, both the nanotemplate and the electrode layer are melted and the barcode-type iron/gold (Fe/Au) multilayer thin film nanowire may be separated.

The diameter of the nanowire may be controlled by using the anodized aluminum nanotemplate having different pore sizes, and a thickness of each layer of the iron and the gold of the nanowire may be controlled by changing the electroplating time.

Further, the operation of substituting the carboxylate substituent on the first segment may be performed by mixing the nanobarcode and the first suspension and reacting the nanobarcode and the first suspension for 8 to 20 hours to 10 to 15 hours. The first suspension may contain an amino acid derivative containing a carboxylate substituent, and specifically, the amino acid derivative may be aminocaproic acid. The carboxylate substituent is substituted in the oxide layer of the iron segment by reacting the nanobarcode with the first suspension as described above, so that the coupling to the substrate may be facilitated.

Further, the operation of mixing the nanobarcode and the second suspension may be performed by stirring the nanobarcode in the second suspension including the integrin ligand peptide (RGD) for 1 to 5 hours or 1 to 3 hours. In this case, the thiolated RGD peptide ligand may be bound to the second segment of the nanobarcode. The solvent may contain any one or more of dimethylformaldehyde (DMF) and dimethyl sulfoxide (DMSO). The integrin ligand peptide is bound to the second segment to tune periodicity and sequence of the ligand of the nanobarcode. Accordingly, it is possible to easily control the adhesion and differentiation of the stem cell by using the nanobarcode.

Further, the present invention provides a method of controlling adhesion and differentiation of stem cells, the method including: manufacturing a nanobarcode-presenting substrate by putting a substrate of which a surface is activated in a solution containing the nanobarcode for controlling adhesion and differentiation of the stem cell; and controlling adhesion and differentiation of the stem cell after treating the nanobarcode-presenting substrate with a culture medium.

b of FIG. 1 is a diagram schematically illustrating the method of controlling adhesion and differentiation of the stem cell according to the exemplary embodiment of the present invention. Referring to b of FIG. 1, it can be seen that the adhesion and mechanosensing of the stem cell are promoted by tuning periodicity and sequences of the integrin ligand peptide bound to the second segment of the nanobarcode to control differentiation.

In particular, the operation of manufacturing the nanobarcode-presenting substrate may include: soaking the surface of the substrate in an acidic solution; and activating the surface of the substrate by putting the soaking-completed substrate in an aminosilane solution.

In the operation of soaking the surface of the substrate in the acidic solution, the surface of the substrate may be soaked in the acidic solution including any one or more of hydrochloric acid and sulfuric acid for 30 minutes to 2 hours or 30 minutes to 1 hour. Accordingly, by binding a hydroxyl group to the surface of the substrate, the activation of the surface of the substrate may be effectively performed so that it is easy to bond with an amino group of the aminosilane solution.

In the operation of activating the surface of the substrate, the surface of the substrate may be activated by putting the substrate in the amino-silane solution. The amino-silane solution may include (3-aminopropyl)triephoxysilane (APTES). In this case, the activation of the surface of the substrate means that the surface of the substrate is positively charged, and particularly, the surface of the substrate may be activated by binding an amine group onto the substrate. The surface of the substrate is positively charged by activating the surface of the substrate by putting the substrate in the amino-silane solution, so that the substrate may be chemically bound to the iron segment of the nanobarcode.

For example, the nanobarcode-presenting substrate may be the substrate obtained by inactivating the surface of the substrate which is not coupled with the nanobarcode by putting the substrate in a solution containing a polyethylene glycol derivative.

The operation of controlling adhesion and differentiation of the stem cell may be performed by changing any one or more of periodicity and sequences of the ligand bound to the nanobarcode of the nanobarcode-presenting substrate.

In particular, in the operation of controlling adhesion and differentiation of the stem cell, in the case where the substrate including the rod-type nanobarcode satisfying Equation 1 below is used, adhesion and mechanosensing differentiation of the stem cell may degrade.

$$[L(M_1M_2)q] \quad \text{[Equation 1]}$$

Herein, $M_1$ is the first segment, $M_2$ is the second segment, q is the number of times of the repetition of the first and second segments, q is an integer between 2 and 10, and L is lengths of the first and second segments.

Further, in the operation of controlling adhesion and differentiation of the stem cell, in the case where the substrate including the rod-type nanobarcode satisfying Equation 2 below is used, adhesion and mechanosensing detection differentiation of the stem cell may be promoted.

$$[L(M_1M_2M_2M_1)q] \quad \text{[Equation 2]}$$

Herein, $M_1$ is the first segment, $M_2$ is the second segment, q is the number of times of the repetition of the first and second segments, q is an integer between 1 and 5, and L is lengths of the first and second segments.

More particularly, in Equation 1, L may be an integer between 10 and 100 or 30 and 75. Further, in Equation 2, L may be an integer between 150 and 500 or 150 and 300, and q may be an integer of between 1 and 2.

For example, in the nanobarcode, Equations 1 and 2 may be represented by any one of $[30(M_1M_2)_{10}]$, $[75(M_1M_2)_4]$, $[75(M_1M_2M_2M_1)_2]$, $[150(M_1M_2)_2]$, $[150(M_1M_2M_2M_1)_1]$, and $[300(M_1M_2)_1]$. In this case, $M_1$ means the first segment and $M_2$ means the second segment. In particular, the nanobarcode may be provided in a rod form satisfying any one of $[30(01)_{10}]$, $[75(01)_4]$, $[75(0110)_2]$, $[150(01)_2]$, $[150(0110)_1]$, and $[300(01)_1]$.

It is possible to effectively control adhesion and differentiation of the stem cell by tuning periodicity and sequences of the integrin ligand peptide on the nanobarcode by binding the integrin ligand peptide to the second segment of the nanobarcode having the foregoing structural formula.

Hereinafter, examples of the present invention will be described. However, the examples below are merely preferable examples of the present invention, and the scope of the present invention is not limited by the examples.

PREPARATION EXAMPLE

Preparation Examples 1 to 6

Prepare nanobarcode

An Fe/Au nanobarcode was prepared to represent various ligand nano-periodicity and ligand sequences on a substrate. As a mold of a pulse electrodeposition process, a porous polycarbonate membrane (PCM) with a pore diameter of 70 nm was used. Silver (Ag) was deposited in the pores of the porous PCM by using an electron beam evaporator. To fill the pores of the PCM with the nanobarcode, a precursor solution was prepared with 0.06 M iron sulfate heptahydrate ($FeSO_4 7H_2O$), 0.01 M potassium dicyanoaurate ($KAu(CN)_2$), and 0.6 M boric acid ($H_3BO_3$). After the pores of the porous PCM are filled with the precursor solution, a pulse current was applied to induce an electrochemical reaction while using a platinum (Pt) plate as a counter electrode.

Due to the significantly different reduction potentials of Fe and Au, Fe and Au were separately deposited in a predetermined order in response to applied pulse currents which are composed of distinctly different current densities. Lengths of the Fe and Au segments were controlled by modulating a pulse duration time.

Six periodically sequenced Fe/Au nanobarcodes with tunable nano-periodicity and the sequence which does not modulate the sizes of the total Fe and Au segments were precisely prepared by optimizing pulse current density and duration time. Four periodically sequenced Fe/Au nanobarcodes were prepared so as to represent tunable Fe and Au nano-periodicity having the same nano-sequence.

Nanobarcode [30(01)$_{10}$] (Preparation Example 1) formed of 30 nm-long Fe and Au segments with 10 repeated sequences was prepared by alternately applying 4 mA/cm$^2$ for 0.7 second and 0.25 mA/cm$^2$ for 9 seconds, respectively. The naming regulation of the structure of the nanobarcode is as follows. The Au and Fe segments were designated as 1 and 0, respectively. In the nanobarcode [30(01)$_{10}$], the length (nm) of each segment was designated as 30, but the repeated sequence of each segment was designated as 10. Nanobarcode [75(01)$_4$] (Preparation Example 2) formed of 75 nm-long Fe and Au segments with four repeated sequences was prepared by alternately applying 4 mA/cm$^2$ for 1.7 seconds and 0.25 mA/cm$^2$ for 22 seconds, respectively. Nanobarcode [150(01)$_2$] (Preparation Example 3) formed of 150 nm-long Fe and Au segment with two repeated sequences was prepared by alternately applying 4 mA/cm$^2$ for 3.6 seconds and 0.25 mA/cm$^2$ for 45 seconds, respectively. 300 nm-long Fe/Au segment [300(01)$_1$] (Preparation Example 4) was prepared by alternately applying 4 mA/cm$^2$ for 7.2 seconds and 0.25 mA/cm$^2$ for 90 seconds, respectively.

To tune nano-periodicity and sequences, two periodically sequenced Fe/Au nanobarcodes were prepared. Nanobarcode [75(0110)$_2$] (Preparation Example 5) formed of a 75-nm-long Fe segment, a 150 nm-long Au segment, and a 75 nm-long Fe segment with two repeated sequences were prepared by alternately applying 4 mA/cm$^2$ for 1.7 seconds, 0.25 mA/cm$^2$ for 44 seconds, and 4 mA/cm$^2$ for 1.7 seconds, respectively. Nanobarcode [150(0110)$_1$] (Preparation Example 6) formed of a 150 nm-long Fe segment, a 300 nm-long Au segment, and a 150 nm-long Fe segment was prepared by alternately applying 4 mA/cm$^2$ for 3.6 seconds, 0.25 mA/cm$^2$ for 90 seconds, and 4 mA/cm$^2$ for 3.6 seconds. Six periodically sequenced Fe/Au nanobarcodes and sequences with tunable nano-periodicity were obtained by physically separating an Ag layer from the porous PCM and chemically removing the porous PCM for 1.5 hours and 0.5 hours with dichloromethane and chloroform, respectively. Subsequently, the nanobarcode was washed three times with acetone and ethanol, and was dispersed in 1 mL of deionized water (DI) before functionalization for substrate coupling.

Comparative Preparation Example 1

A nanobarcode was prepared by the same method as that of Preparation Example 1 except that a negatively charged thiolated RGD peptide (CDDRGD, GL Biochem) was not added.

EXAMPLE

Examples 1 to 6

Manufacture Nanobarcode-Presenting Substrate

The six periodically sequenced nanobarcodes prepared in Preparation Examples 1 to 6 were chemically functionalized and grafted to a substrate to express various nano-periodicity of ligand sequences. Since it is well known that the amine group may be coupled to a natural oxide layer, the amine group of aminocaproic acid was used to be coupled to the natural oxide layer of the iron (Fe) segment in the nanobarcode to represent the carboxylate group after surface functionalization. A mixed solution of 1 mL of nanobarcode and 1 mL of 6 mM aminocaproic acid solution was stirred at a room temperature for 12 hours, and then centrifuged and washed with deionized water. A 22 mm×22 mm flat cell culture grade glass substrate was aminated to allow the carboxylate groups on the surfaces of the six different nanobarcodes to bind to the amine groups on the substrate. The substrate was first washed with a mixture in which hydrochloric acid and methanol were mixed at a ratio of 1:1 and rinsed with deionized water. The substrate was soaked in sulfuric acid for 1 hour to activate the hydroxyl group and rinsed with deionized water. The substrate was aminated for 1 hour in 3-aminopropyl triethoxy silane (APTES) and ethanol (1:1) in a darkroom and washed with ethanol, followed by drying for 1 hour at 100° C. The aminocaproic acid-bound six periodically sequenced nanobarcodes in 1 mL of deionized water were activated through the EDC/NHS reaction for 3 hours in 0.5 mL of 20 mM N-ethyl-N'-(3-(dimethylaminopropyl) carbodiimide) (EDC) and 0.5 mL of 20 mM N-hydroxysuccinimide (NHS), and then washed with deionized water.

The six periodically sequenced nanobarcodes were coupled to the aminated substrate to present the tunable ligand nano-periodicity and sequences by precisely optimizing nanobarcode concentration (1 to 2 mL) and reaction time (2 to 3 h) in the six periodically sequenced nanobarcodes with maintaining constant the substrate-coupled nanobarcode and the ligand density. The thiolated RGD peptide ligand was grafted to the Au segment on the nanobarcode-coupled substrate. The nanobarcode-coupled substrate was cultured for 2 hours by using 0.2 mM thiolated RGD peptide ligand (GCGYCFCDSPG, GLBiochem) in dimethylsulfoxide (DMSO) with 0.25% N,N-diisopropylethylamine (DIPEA) and 10 mM tris(2-carboxyethyl)phosphine hydrochloride (TCEP), and then washed with deionized water. Non-RGD ligand-specific stem cell adhesion was minimized by blocking the non-nanobarcode-coated areas on the substrate with 100 mM-methoxy-poly(ethylene glycol)-succinimidyl carboxymethyl ester with 0.2% N,N-diisoprophyl-ethylamine (DIPEA) in deionized water for 2 hours in the dark condition and then washed with deionized water.

Comparative Example 1

A nanobarcode-presenting substrate was manufactured with the same method except that the nanobarcode prepared in Comparative Example 1 was used.

EXPERIMENTAL EXAMPLE

Experimental Example 1

Figure 6:
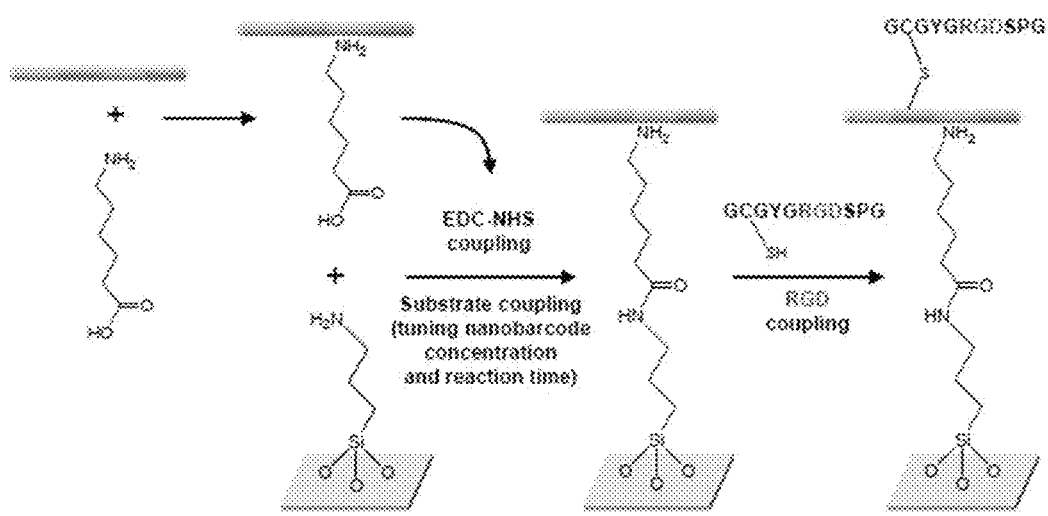
FIG. 6 is an image schematically illustrating operations for manufacturing a substrate including the nanobarcode according to the exemplary embodiment of the present invention.

To check the form and the chemical characteristic of the nanobarcode according to the present invention, high-angle annular dark field scanning transmission electron microscopy (HAADF-STEM) analysis, energy dispersive spectroscopy (EDS) analysis, X-ray diffraction (XRD) analysis, vibrating sample magnetometry (VSM), and Fourier transform infrared spectroscopy (FT-IR) analysis were performed on the prepared nanobarcode, and the result thereof is represented in FIGS. 2 and 6.

In particular, to characterize the sizes and the shapes of the six periodically sequenced Fe/Au nanobarcodes with tunable nano-periodicity and sequences, the HAADF-STEM imaging was performed according to the previously demonstrated procedure. The HAADF-STEM imaging was conducted at 200 kV by using a probe Cs-corrected JEM ARM200CF (JEOL Ltd.) under spherical aberration (C3) of 0.5 to 1.0 μm resulting in a phase of 27 to 28 mrad. The convergence semi-angle for imaging was 21 mrad whereas the collection semi-angle for HAADF was 90-370 mrad. Micrographs were acquired at electron probe sizes of 8C & 9C (JEOL defined), which were measured to be 1.28 and 1.2 Å, respectively, and a pixel dwell time of 10-15 μs with 2048×2048 pixel area. When an emission current of 8-13 μA is used, a probe current range of 10-20 Pa is calculated. A 40 μm aperture was used, which yielded a beam convergence semi-angle of α=27.5 mrad. The electron dose introduced per image varied in around 1,000-2,000 e/Å2 depending on the magnification. In the obtained image, darker and brighter shapes represent Fe and Au segments, respectively. The nanoscale dimensions (length, diameter, and surface area) of each or total Fe and Au segments with sharp interfaces in the nanobarcode were calculated by using HADDF-STEM imaging. Through the calculation, it was confirmed that the six periodically sequenced Fe/Au nanobarcodes with tunable nano-periodicity and sequences have the similar dimensions of the total Fe and Au segments. The Fe and Au segments with sharp interfaces in the six periodically sequenced Fe/Au nanobarcodes were specifically identified through EDS mapping using two SOD detectors (Thermo Fisher Scientific). The Fe and Au element mapping was individually used for identifying the Fe and Au segment in the six periodically sequenced Fe/Au nanobarcodes with tunable nano-periodicity and sequences obtained by strictly individually modulating a pulse, a current segment, and a duration time.

The co-existence of Fe and Au segments repeated in the six periodically sequenced nanobarcodes was confirmed by carrying out the X-ray diffraction analysis (D/MAX-2500V/PC, Rigaku). The peaks were assigned with crystalline indices of the Fe and Au phases present in the six periodically sequenced nanobarcodes by using Powder Diffraction File (PDF) data of the Fe phase (PDF #870722) and the Au phase (PDF #040784).

The magnetic properties of the Fe segments in the six periodically sequenced nanobarcodes were analyzed through vibrating sample magnetometry (VSM) measurement under an applied magnetic field (H) at a room temperature. The corresponding magnetic moment (M) is indicated with hysteresis loops after normalization to the maximum value of the magnetic moment in each nanobarcode.

FIG. 2 is high-angle annular dark field scanning transmission electron microscopy (HAADF-STEM) image, and energy dispersive spectroscopy (EDS) and field emission scanning electron microscopy (FE-SEM) image of a nanobarcode according to the exemplary embodiment of the present invention. Referring to FIG. 2, the Fe and Au segments alternating in the HAADF-STEM image were identified with dark and bright contrast areas, and it was confirmed that the Fe and Au segments have the sharp interfaces without alloy formation through the EDS mapping image for each Fe and Au element.

Referring to b of FIG. 2, the nano sizes (length, diameter, and surface area) of each or total Fe and Au segments were accurately quantified in the nanobarcode. In particular, the length of each Fe/Au segment in the nanobarcode was represented with 30.8±0.3 nm/28.1±1.8 nm in [30(01)$_{10}$] group, 72.3±1.4 nm/74.6±4.3 nm in [75(01)$_4$] group, 132.7±19.2 nm/142.5±6.1 nm in [150(01)2] group, 310.7±13.0 nm/294.7±9.5 nm in [300(01)$_1$] group, 69.3±3.0 nm/149.7±13.7 nm in [75(0110)2] group, and 154.2±1.3 nm/302.1±3.6 nm in [150(0110)$_1$] group. Through this, it was seen that the nano-periodicity and sequences were systematically tuned in the six different nanobarcodes by precisely regulating pulse current density and duration while the nano-periodicity and sequences were synthesized.

Figure 3:
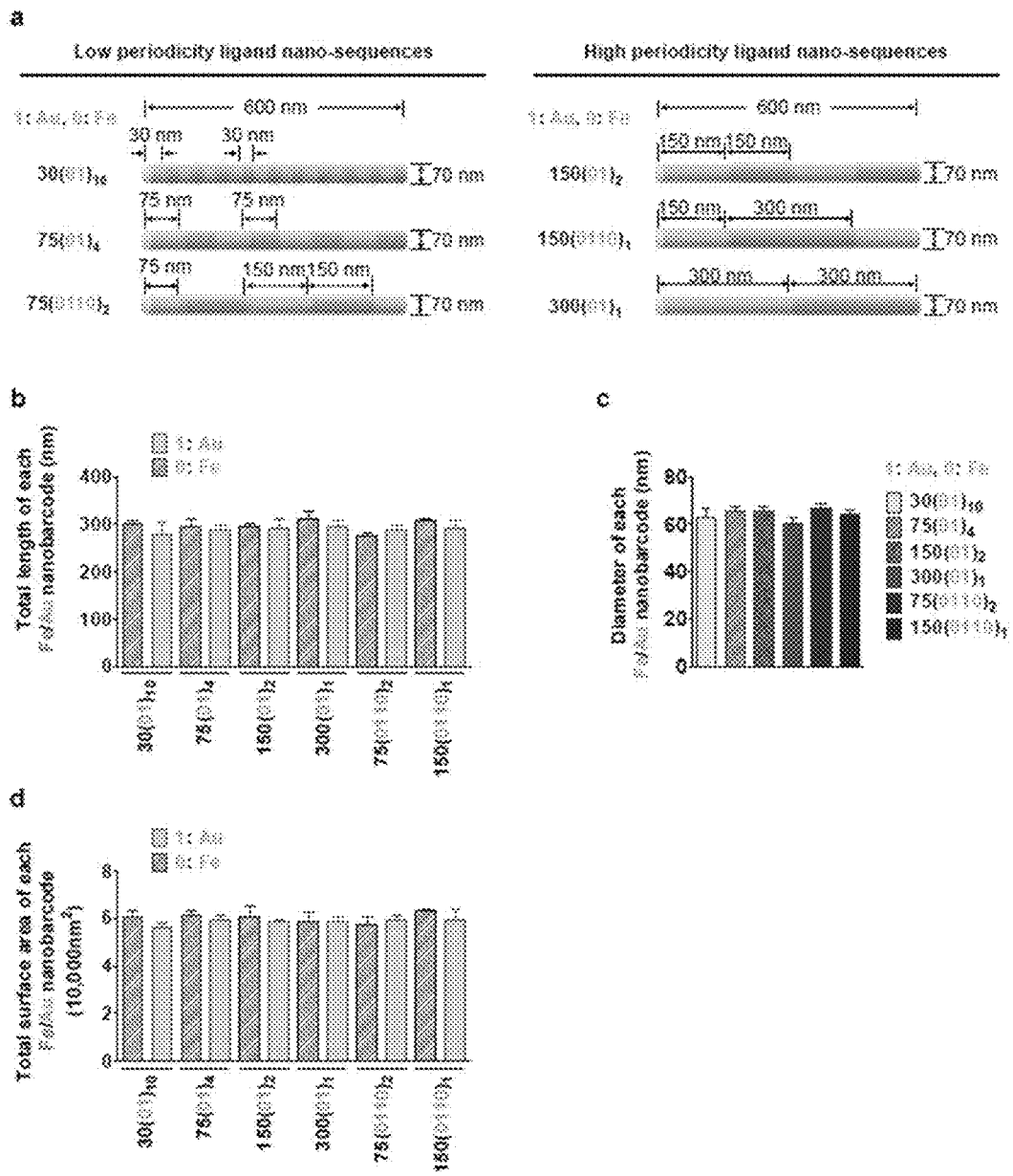
FIG. 3 is a schematic diagram (a) of the nanobarcode according to the exemplary embodiment of the present invention, and graphs illustrating a total length (b), a diameter (c), and a surface area (d) of each of Fe/Au nanobarcodes calculated from the result of the HAADF-STEM.

FIG. 3 is a schematic diagram (a) of the nanobarcode prepared in the present invention, and graphs illustrating a total length (b), a diameter (c), and a surface area (d) of each of Fe and Au nanobarcodes calculated from the result of the HAADF-STEM. Referring to FIG. 3, in contrast, total lengths of Fe vs. Au segment in each nanobarcode ranged from 270.7 to 306.2 nm vs. from 279.9 to 289.1 nm, respectively, in the six different nanobarcodes without significant differences. The diameters of each Fe/Au nanobarcode ranged from 63.2 to 66.9 nm in the six different nanobarcodes without significant differences. The total surface area of the Fe vs. Au segment in each nanobarcode ranged from 57500 to 61420 $nm^2$ vs. from 56270 to 60330 $nm^2$, respectively, in the six different nanobarcodes without significant differences. These results collectively indicate that the six periodically sequenced Fe/Au nanobarcodes were precisely prepared to display the tunable ligand nano-periodicity and sequences without modulating the dimensions of total Fe and Au segments. In this case, Au and Fe segments were referred to as 1 and 0 in parentheses, respectively, and the length (nm) of each Au and Fe segment was referred to as 30, 75, 150, and 300.

Figure 4:
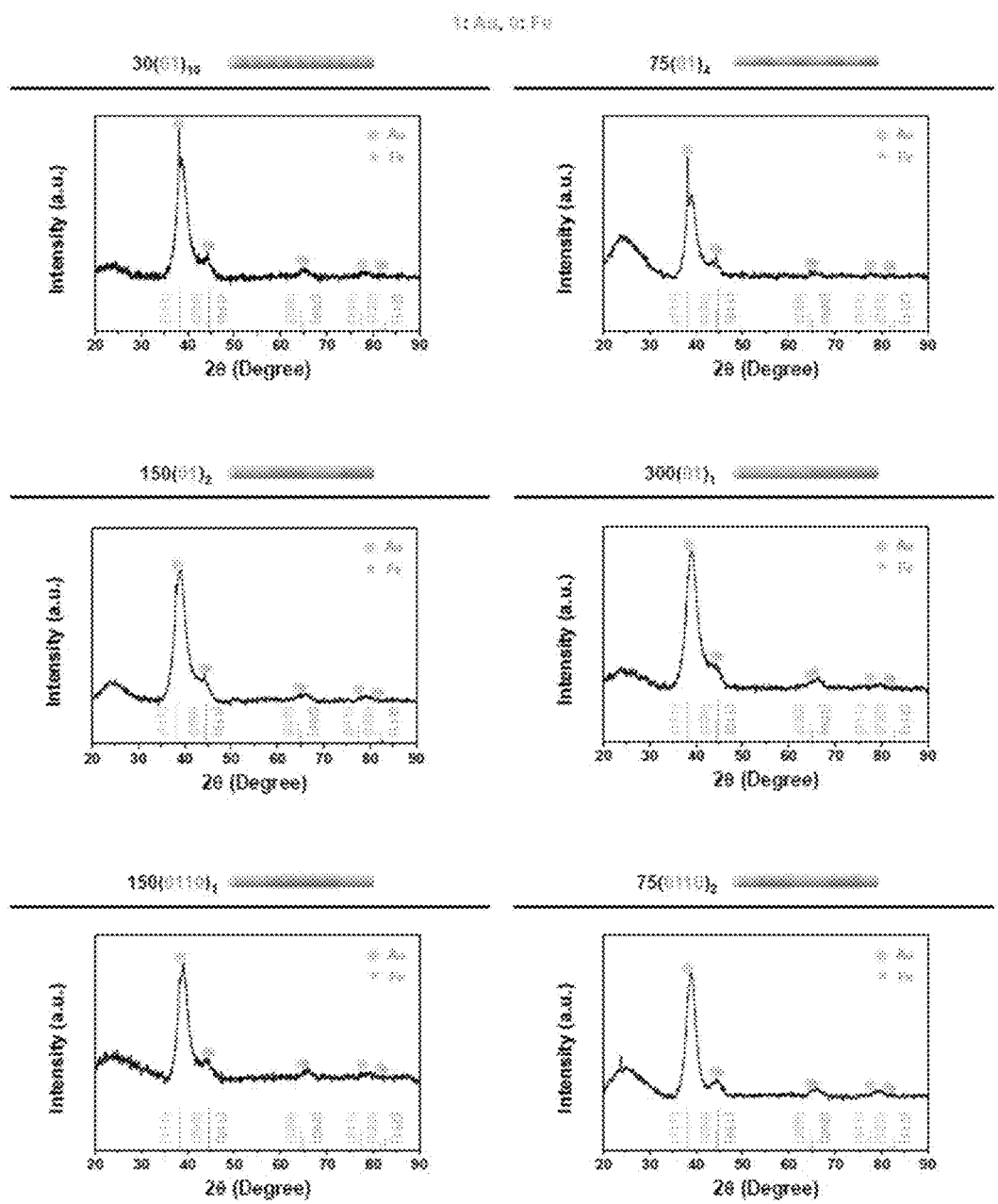
FIG. 4 is an X-ray diffraction analysis graph of a nano barcode according to the exemplary embodiment of the present invention.

FIG. 4 is an X-ray diffraction analysis graph of a nanobarcode according to the exemplary embodiment of the present invention. Referring to FIG. 4, the crystalline phases of the Fe and Au segments in nanobarcodes were analyzed via X-ray diffraction, which revealed that diffraction peaks corresponding to the Fe and Au phases were similarly co-present in the six different nanobarcodes. Through this, it can be seen that the six periodically sequenced Fe/Au nanobarcodes exhibit the similar property.

Figure 5:
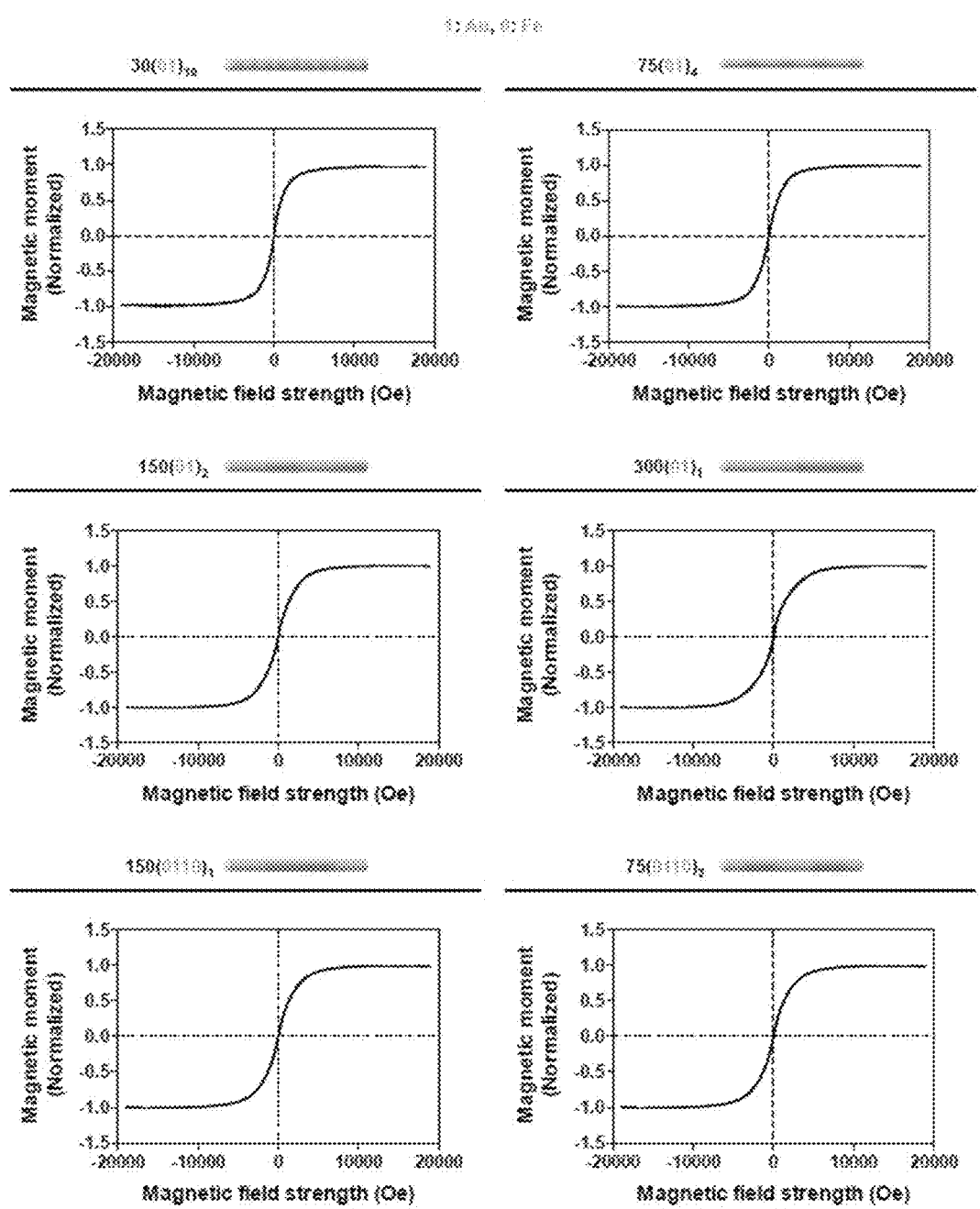
FIG. 5 is a graph illustrating a measurement result of a vibrating sample magnetometry (VSM) of the nanobarcode according to the exemplary embodiment of the present invention.

FIG. 5 is a graph illustrating a measurement result of the VSM of the nanobarcode according to the exemplary embodiment of the present invention. In particular, the magnetic properties of nanobarcodes due to the presence of the Fe segments were analyzed, revealing that all of six different nanobarcodes exhibit similar magnetic behaviors without obvious hysteresis. This magnetic property may be utilized for the reversible remote control of the nanobarcodes of the present invention by using an external magnetic field.

Experimental Example 2

Figure 7:
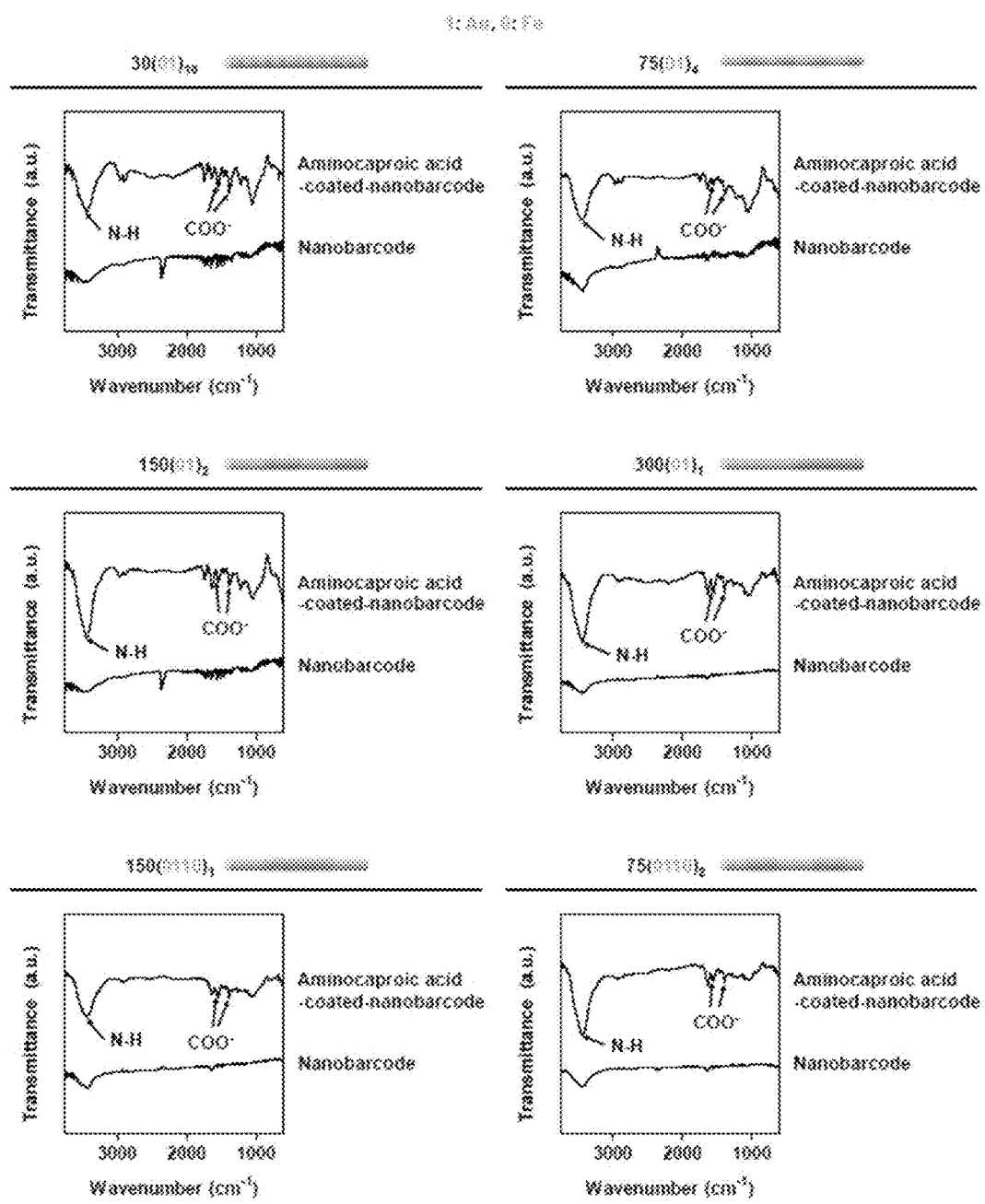
FIG. 7 is a diagram illustrating a result of a Fourier transform infrared spectroscopy (FT-IR) analysis of the nanobarcode according to the exemplary embodiment of the present invention.

To check the property of the substrate including the nanobarcode according to the present invention, the substrate including the nanobarcode was photographed with the FE-SEM and the FT-IR was carried, and the results thereof are represented in b of FIG. 2 and FIG. 7.

The FT-IR was conducted by using GX1 (Perkin Elmer Spectrum, USA) to confirm the chemical bond characteristics of the nanobarcode. The samples subjected to the analysis of changes in chemical bond characteristics were lyophilized and densely packed into KBr pellet prior to the analysis.

FIG. 6 is an image schematically illustrating operations for manufacturing a substrate including the nanobarcode according to the exemplary embodiment of the present invention. Referring to FIG. 6, the six periodically sequenced nanobarcodes was chemically functionalized before being grafted to the substrate. The amine group of aminocaproic acid was coupled to a natural oxide layer of the Fe segment of the nanobarcode to display a carboxylate group. Various ligand nano-periodicities and sequences were confirmed without modulating the nanobarcode coupled to the substrate and the ligand density by precisely optimizing a concentration and reaction time of the nanobarcode by activating the carboxylate group in the aminocaproic acid-coated nanobarcode and grafting the nanobarcode onto the aminated substrate. Subsequently, thiolated RGD ligands were grafted to Au segments in the nanobarcode-coupled substrate. The density of the substrate-coupled ligand-presenting nanobarcode, as well as the dimensions of the total Fe and Au segments, are similarly maintained, to separate the effect of ligand density for the substrate.

Referring to b of FIG. 2, the substrate-coupled ligand-presenting nanobarcodes were visualized by using field emission scanning electron microscopy, which revealed their uniform distribution in a monolayer. Their densities ranged from 0.0235 to 0.0277 per $\mu m^2$, thereby confirming the successful maintenance of a similar density in all of the substrate-coupled ligand-presenting nanobarcodes without significant differences. Through the following experiment, it was confirmed that the density may efficiently control the cell adhesion and differentiation of stem cells.

FIG. 7 is a diagram illustrating a result of a Fourier transform infrared spectroscopy (FT-IR) analysis of the nanobarcode according to the present invention. Referring to FIG. 7, it can be seen the chemical bond characteristics of the aminocaproic acid-coated nanobarcodes. In particular, COO bonds were revealed at 1560 to 1565 $cm^{-1}$ and 1387 to 1389 $cm^{-1}$ and N—H bonds were revealed at 3432 to 3448 $cm^{-1}$. Through this, it is confirmed that the aminocaproic acid was successfully coupled to the six different nanobarcodes.

Experimental Example 3

To check an influence of the nano-periodicity and ligand sequences of the nanobarcode according to the present invention to the adhesion of the stem cells, the following experiment was conducted, the result of which is represented in FIGS. 8 to 11.

The effect of tuning the ligand nano-periodicity and sequences for focal adhesion, mechanosensing, and differentiation of stem cells was evaluated by using the nanobarcode-presenting substrate. The substrate was subjected to sterilization under ultraviolet light for 1 hour prior to the use of the substrate. Human mesenchymal stem cells (hMSCs, passage 5 from Lonza) were plated onto the sterilized substrates at a plating density of approximately 9,500 cells/$cm^2$ and cultured in growth medium at 37° C. under 5% $CO_2$. The focal adhesion and mechanosensing of the stem cells were evaluated while tuning nano-periodicity alone in the nanobarcode of ligand sequences: [30(01)$_{10}$], [75(01)$_4$], [150(01)$_2$], and [300(01)$_1$] according to the present invention. Further, the focal adhesion and mechanosensing of the stem cells were evaluated while tuning both nano-periodicity and ligand sequences by using the nanobarcode of the ligand sequences [75(01)$_4$], [75(0110)$_2$], [150(01)$_2$], and [150(0110)$_1$]. Further, the effect of nano-periodicity in the RGD ligand sequences on the control of focal adhesion of the stem cells was evaluated by using the substrate with tunable nano-periodicity in the scrambled ligand (RAD).

The mechanotransduction-mediated differentiation of the stem cells was evaluated under the tuning of nano-periodicity by using the groups of [75(01)$_4$], [75(0110)$_2$], and [300(01)$_1$] with inhibitors of ROCK (50 μM Y27632), myosin II (10 μM blebbistatin), or actin polymerization (2 μg/mL cytochalasin D). The differentiation of adherent stem cells was evaluated under the tuning of both high nano-periodicity and ligand sequences after osteogenic induction medium culturing.

Figure 8:
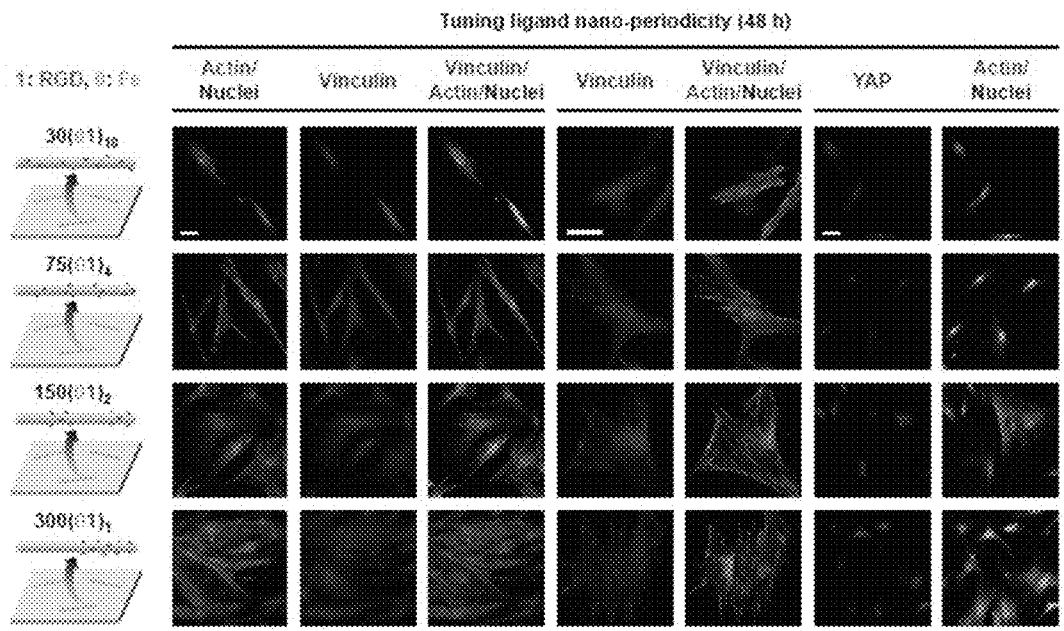
FIG. 8 is an immunofluorescent confocal image of stem cells cultured for 48 hours by using the nanobarcode according to the exemplary embodiment of the present invention against F-actin, nucleus, vinculin, and YAP, and in this case, a scale bar represents 20 µm.
Figure 8:
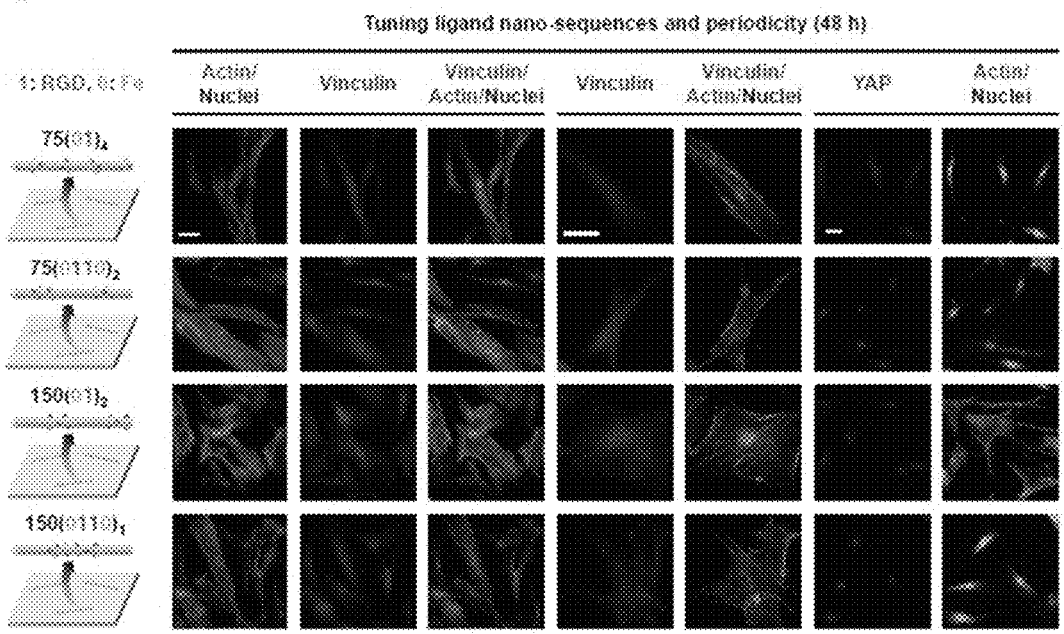

FIG. 8 is an immunofluorescent confocal image of stem cells cultured for 48 hours by using the nanobarcode according to the present invention against F-actin, nucleus, vinculin, and YA, and in this case, a scale bar represents 20 μm. a of FIG. 8 illustrates the case where nano-periodicity is tuned, and b of FIG. 8 illustrates a result of the case where nano-periodicity and ligand sequences are tuned.

Figure 9:
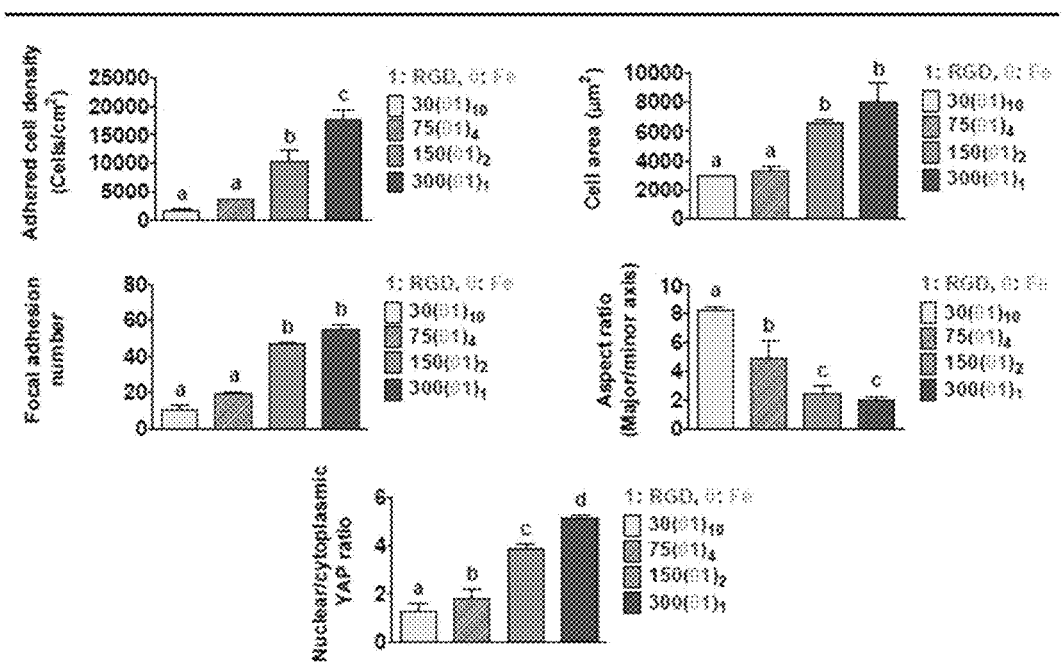
FIG. 9 is a graph illustrating a result of quantification of the stem cells cultured for 48 hours in adherent cell density, spread area, focal adhesion number, aspect ratio (major/minor axis ratio), and nuclear/cytoplasmic YAP ratio from immunofluorescent confocal image data.

FIG. 9 is a graph illustrating a result of quantification of the stem cells cultured for 48 hours in adherent cell density, cell spread area, focal adhesion number, aspect ratio (major/minor axis ratio), and nuclear/cytoplasmic YAP ratio from the immunofluorescent confocal image data of a of FIG. 8.

Referring to a of FIG. 8 and FIG. 9, the immunofluorescent confocal images revealed that stem cells adhered more strongly and spread of stem cells is promoted with increasing (from 30 to 300) nano-periodicity presentation in ligand sequences. This was confirmed by the cell density, the spread area, the focal adhesion number, and the vinculin expression. Through this, it can be seen that the group with high ligand nano-periodicity of the nanobarcode according to the present invention promotes focal adhesion to stimulate nuclear translocation of YAP mechanotransduction of stem cells.

Figure 10:
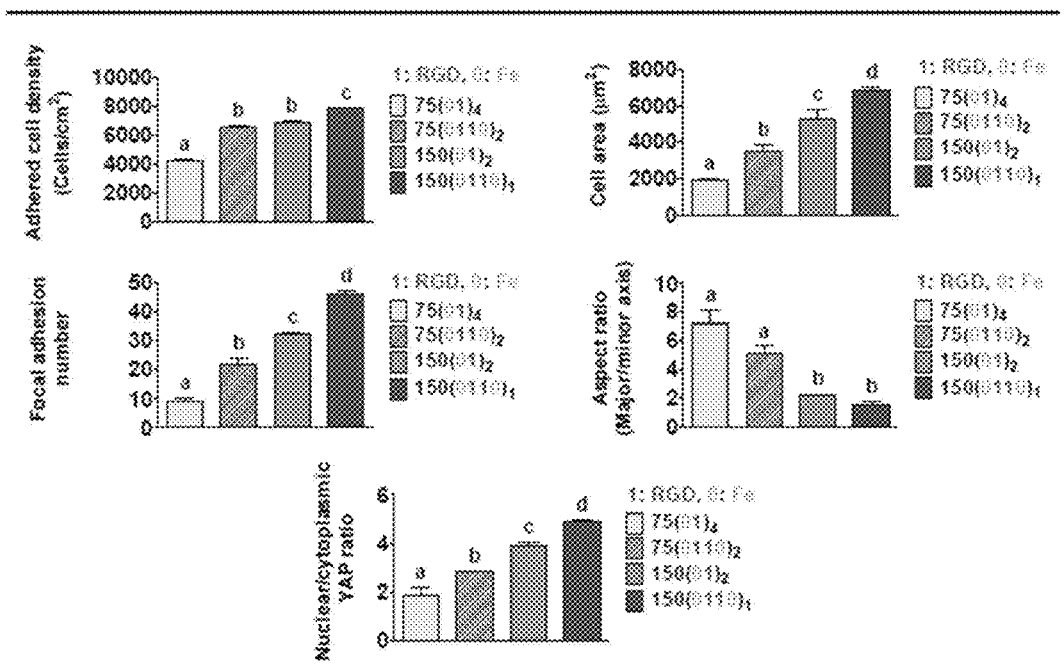
FIG. 10 is a graph illustrating a result of quantification of stem cells cultured for 48 hours in adherent cell density, cell spread area, focal adhesion number, aspect ratio (major/minor axis ratio), and nuclear/cytoplasmic YAP ratio from immunofluorescent confocal image data.

FIG. 10 is a graph illustrating a result of quantification of the stem cells cultured for 48 hours in adherent cell density, cell spread area, focal adhesion number, aspect ratio (major/minor axis ratio), and nuclear/cytoplasmic YAP ratio from the immunofluorescent confocal image data of b of FIG. 8.

Figure 11:
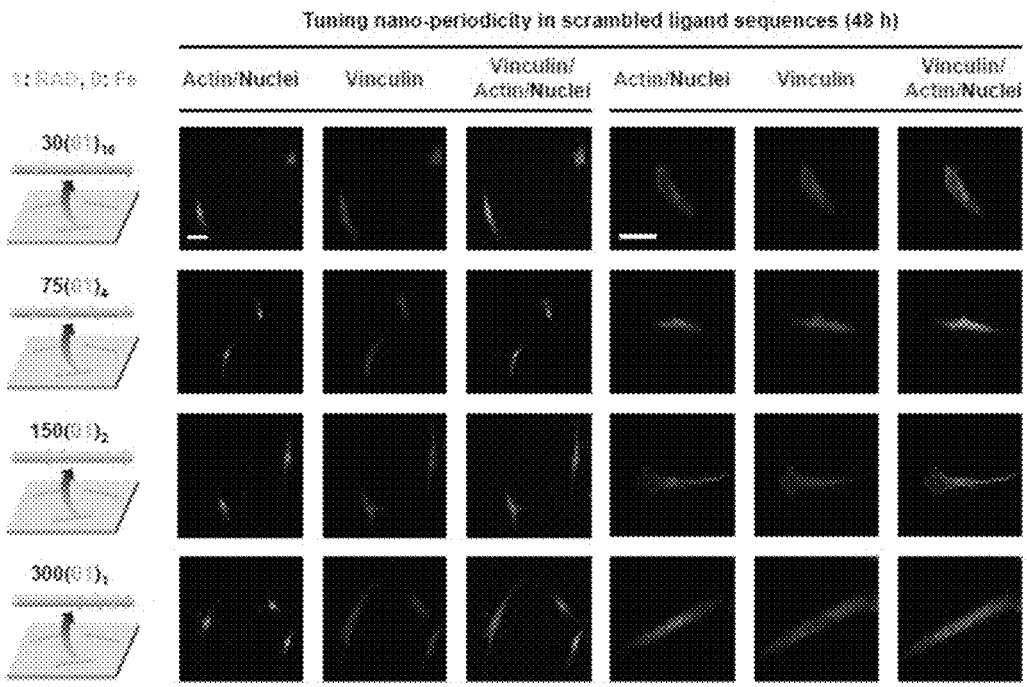
FIG. 11 is an immunofluorescent confocal image (a) of stem cells cultured for 48 hours by using scrambled RAD according to a Comparative Example of the present invention against F-actin, nucleus, vinculin, and YAP, and in this case, a scale bar represents 50 μm. b of FIG. 11 is a graph illustrating a result of quantification of the stem cells cultured for 48 hours in adherent cell density, cell spread area, focal adhesion number, aspect ratio (major/minor axis ratio), and nuclear/cytoplasmic YAP ratio from immunofluorescent confocal image data.
Figure 11:
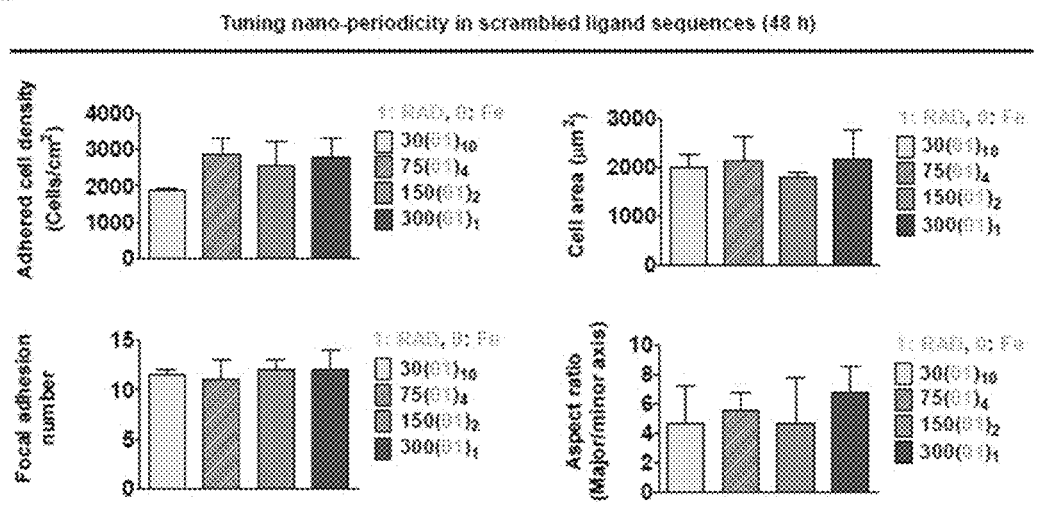

FIG. 11 is an immunofluorescent confocal image (a) of stem cells cultured for 48 hours by using scrambled RAD ligands according to a Comparative Example of the present invention against F-actin, nucleus, vinculin, and YAP, and in this case, a scale bar represents 50 μm. b of FIG. 11 is a graph illustrating a result of quantification of the stem cells cultured for 48 hours in adherent cell density, cell spread area, focal adhesion number, aspect ratio (major/minor axis ratio), and nuclear/cytoplasmic YAP ratio from the immunofluorescent confocal image data. Referring to FIG. 11, it was confirmed that the tuning of nano-periodicity in the scrambled RAD ligand sequences did not affect adhesion of stem cells.

Referring to b of FIG. 8 and FIG. 11, four different nanobarcode groups in which both nano-periodicity and ligand sequences are tuned were prepared: [75(01)$_4$], [75(0110)$_2$], [150(01)$_2$], and [150(0110)$_1$]. The nanobarcode with high nano-periodicity promoted focal adhesion and mechanosensing performance of stem cells. [150(0110)$_1$] vs. [75(0110)$_2$] and [150(01)$_2$] vs. [75(01)$_4$]. This confirmed that the nanobarcode with high ligand nano-periodicity exhibited enhanced cell adhesion with closer ligand presentation without modulating ligand density. In particular, it was confirmed that by changing the ligand sequences alone in the nanobarcode with the same nano-periodicity, ligand that is available only at the end sequence of nanobarcode [150(01)$_2$] stimulated focal adhesion and mechanosensing of stem cells compared to ligand that is available only in the inner sequence of nanobarcode [75(0110)$_2$]. Through this, it can be seen that it is possible to regulate cellular adhesion by modulating nanobarcode ligand spacing with different ligand sequences.

Therefore, it is possible to regulate adhesion of stem cells by modulating a ligand location in the sequences and the ligand spacing of the nanobarcode.

Experimental Example 4

The experiment on whether the tuning of the nano-periodicity of the ligand sequences by using the nanobarcode according to the present invention controls the phenotypic polarization-mediated adhesion of stem cells was conducted as described below, and the results are represented in FIGS. 12 to 18.

The focal adhesion and mechanosensing of stem cells regulate their osteogenic differentiation, which was evaluated among groups with nano-periodicity in ligand sequences: $[75(01)_4]$, $[75(0110)_2]$, and $[300(01)_1]$.

Figure 12:
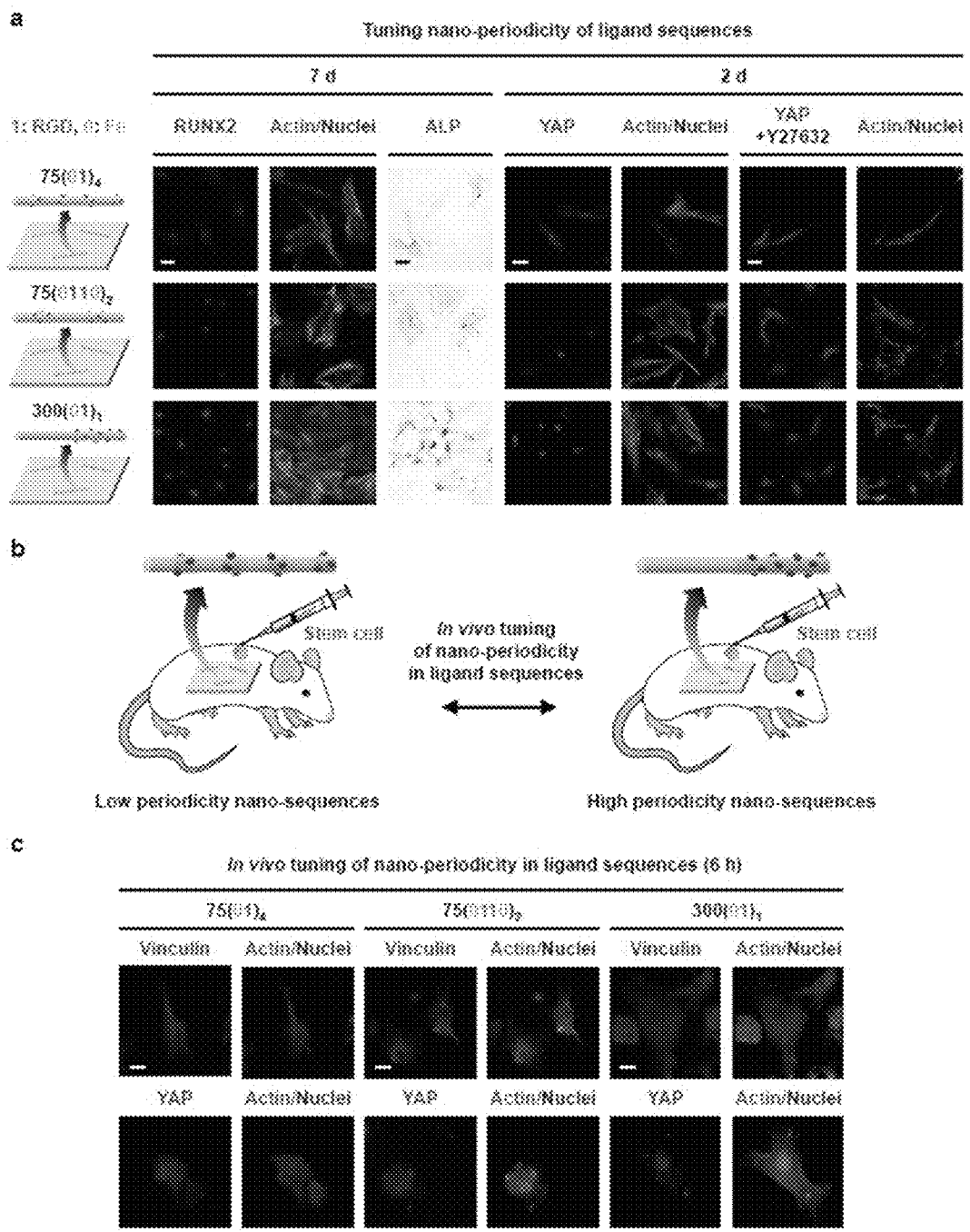
FIG. 12 is a diagram illustrating an experimental result for mechanotransduction of stem cells in vitro and in vivo by tuning nano-periodicity in ligand sequences by using the nanobarcode.

FIG. 12 is a diagram illustrating an experimental result for mechanotransduction of stem cells in vitro and in vivo by tuning nano-periodicity in ligand sequences by using the nanobarcode according to the present invention. a of FIG. 12 is an immunofluorescent confocal image of RUNX2, F-actin, nuclei, and YAP with ROCK inhibition (Y27632), and ALP staining, and in this case, the scale bar is 50 μm. b of FIG. 12 is a schematic diagram illustrating the case where the substrate including the nanobarcode with ligand nano-periodicity in vivo is subcutaneously implanted and then hMSC is injected. c of FIG. 12 is an immunofluorescent confocal image of vinculin, F-actin, nuclei, and YAP in the case where the hMSC is injected, and in this case, the scale bar is 20 μm.

Figure 13:
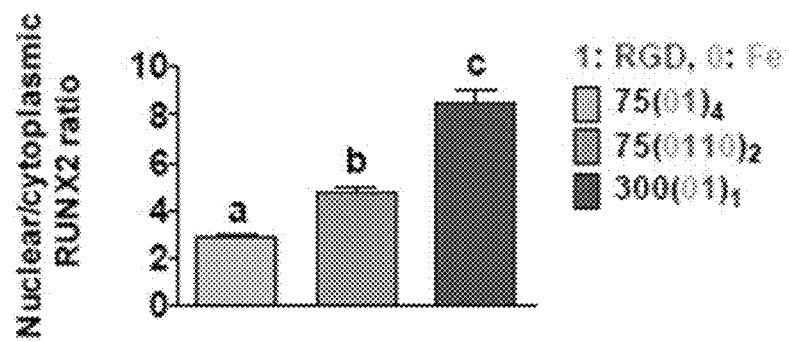
FIG. 13 is a graph illustrating a result of a quantification analysis of a nuclear/cytoplasmic RUNX2 fluorescence ratio and alkaline phosphatase-positive cells after stem cells are cultured on a substrate including the nanobarcode with nano-periodicity for 7 days, based on an immunofluorescent confocal image by using the nanobarcode according to the present invention.
Figure 13:
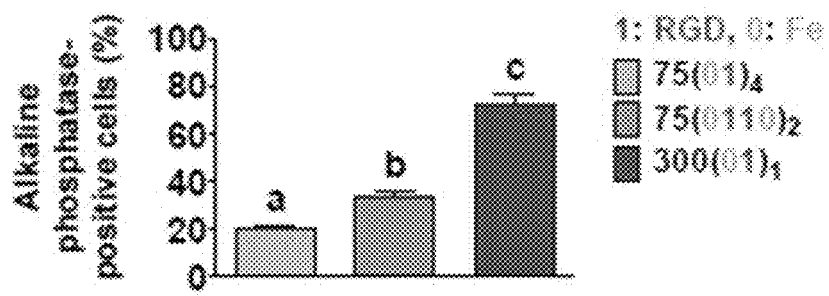
Figure 13:
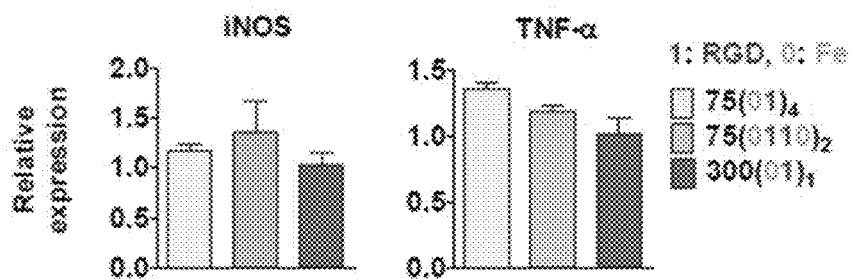

FIG. 13 is a graph illustrating a result of a quantification analysis of a nuclear/cytoplasmic RUNX2 fluorescence ratio and alkaline phosphatase-positive cells after stem cells are cultured on a substrate including the nanobarcode with nano-periodicity for 7 days, based on the immunofluorescent confocal image of a of FIG. 12.

Figure 14:
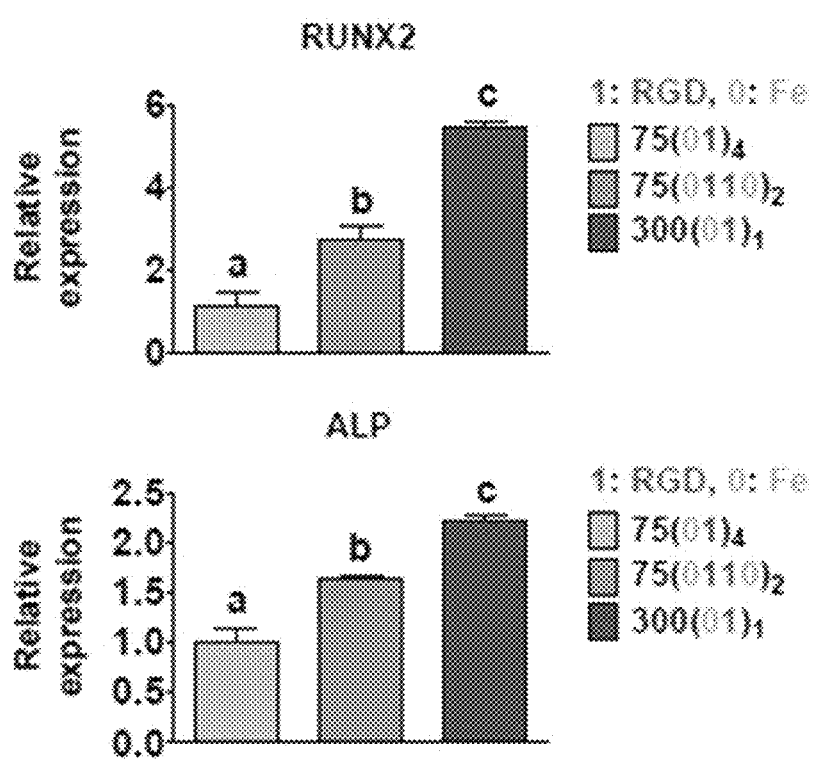
FIG. 14 is a graph illustrating a result of a quantification analysis of a nuclear/cytoplasmic RUNX2 and ALP genes expression profile after stem cells are cultured on a substrate including the nanobarcode with nano-periodicity for 7 days, based on an immunofluorescent confocal image by using the nanobarcode according to the exemplary embodiment of the present invention.

FIG. 14 is a graph illustrating a result of a quantification analysis of a nuclear/cytoplasmic RUNX2 and ALP genes expression profile after stem cells are cultured on a substrate including the nanobarcode with nano-periodicity for 7 days, based on the immunofluorescent confocal image of a of FIG. 12.

Referring to a of FIG. 12, FIG. 13, and FIG. 14, it can be seen that the high nano-periodicity of the ligand sequences facilitates mechanotransduction of stem cells in vitro and in vivo to control differentiation of stem cells.

Figure 15:
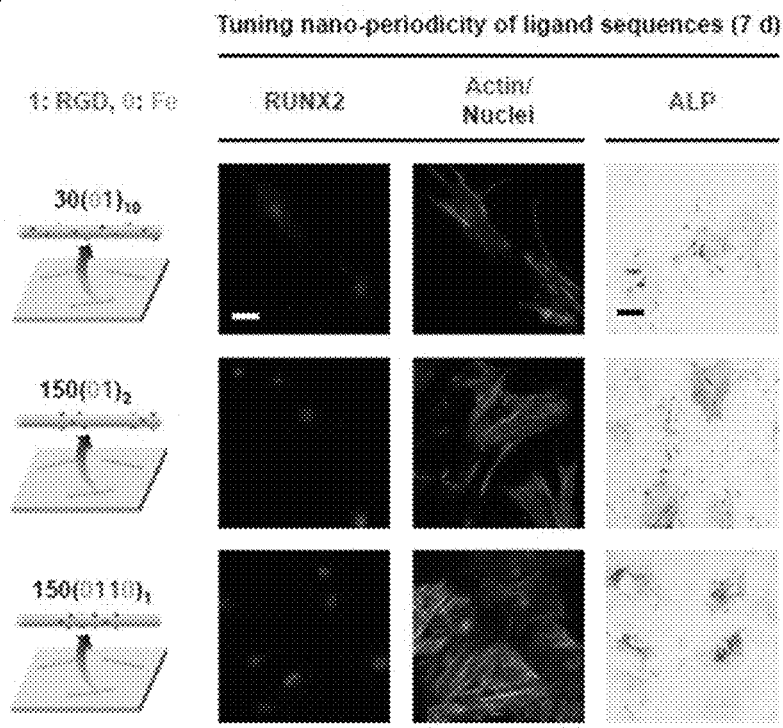
FIG. 15 is a diagram illustrating an experimental result for mechanotransduction of stem cells in vitro by tuning nano-periodicity in ligand sequences and ligand sequences by using the nanobarcode according to the exemplary embodiment of the present invention.
Figure 15:
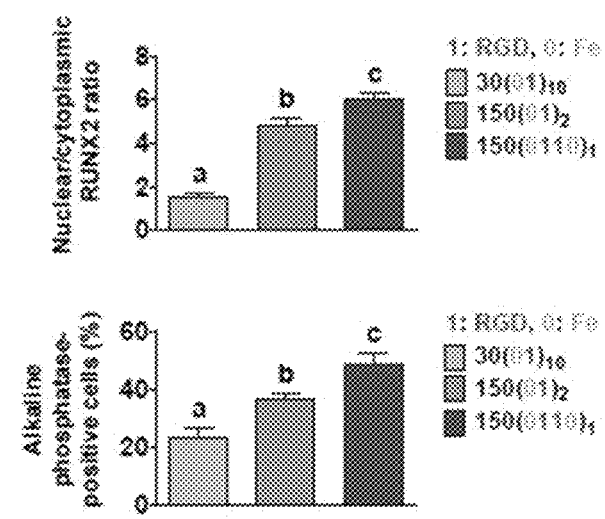

FIG. 15 is a diagram illustrating an experimental result for mechanotransduction of stem cells in vitro by tuning nano-periodicity in ligand sequences and ligand sequences by using the nanobarcode according to the present invention. a of FIG. 15 is an immunofluorescent confocal image of RUNX2, F-actin, nuclei, and YAP with ROCK inhibition (Y27632), and ALP staining, and in this case, the scale bar is 50 μm. b of FIG. 15 is a graph illustrating a result of a quantification analysis of a nuclear/cytoplasmic RUNX2 fluorescence ratio and alkaline phosphatase-positive cells after stem cells are cultured on a substrate including the nanobarcode with nano-periodicity for 7 days. Referring to FIG. 15, the differentiation of the stem cells is facilitated by high nano-periodicity in the ligand sequences: $[30(01)_{10}]$, $[150(0110)_1]$, and $[150(01)_2]$.

Figure 16:
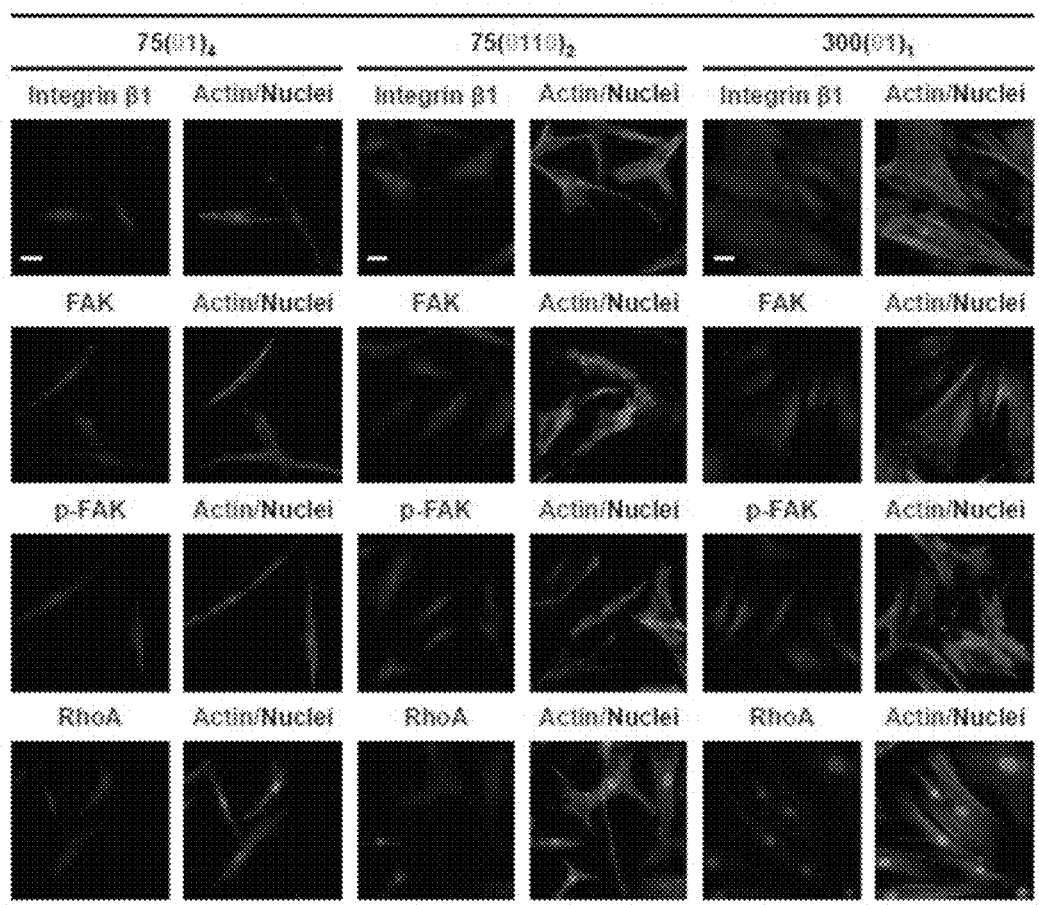
FIG. 16 is an immunofluorescent confocal image of stem cells cultured for 48 hours by using the nanobarcode according to the exemplary embodiment of the present invention against integrin β1, FAK, p-FAK, RhoA, F-actin, and nucleus.

FIG. 16 is an immunofluorescent confocal image of stem cells cultured for 48 hours by using the nanobarcode according to the present invention against integrin β1, FAK, p-FAK, RhoA, F-actin, and nucleus. Referring to FIG. 16, the case where the nanobarcode with high nano-periodicity is included activated integrin β1, which serially stimulates intracellular mechanosensitive signaling via focal adhesion kinase (FAK) and its phosphorylation (p-FAK) that activates RhoA and TAZ mechanotransduction.

Figure 17:
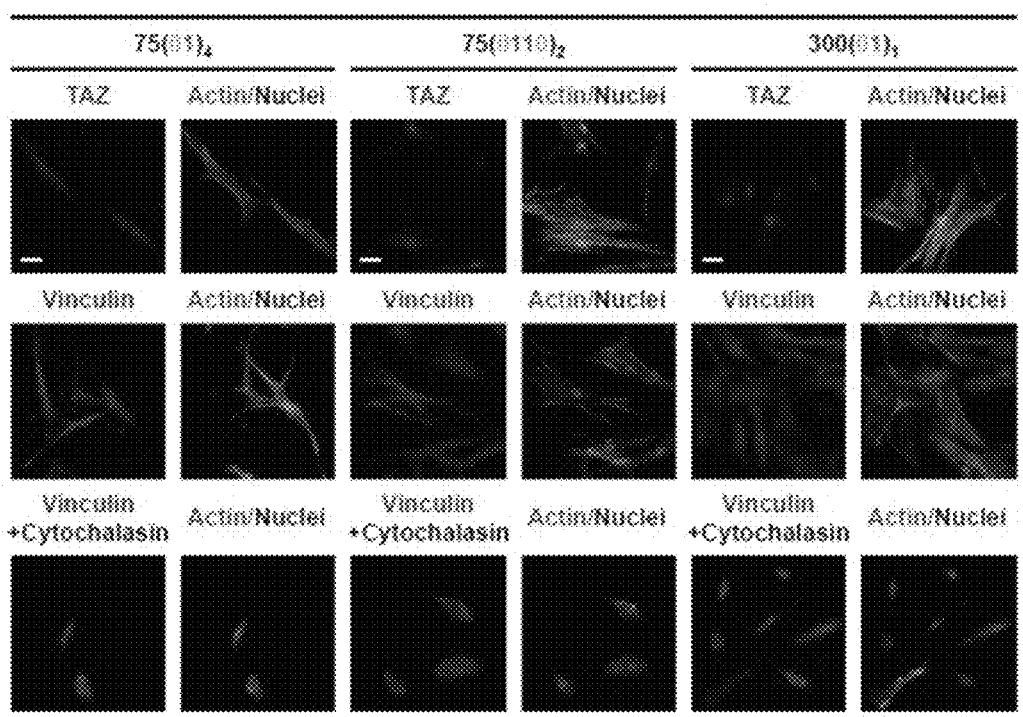
FIG. 17 is an immunofluorescent confocal image (a) of stem cells having actin polymerization inhibitor (cytochalasin D) cultured for 48 hours by using the nanobarcode according to the exemplary embodiment of the present invention against TAZ, vinculin, F-actin, and nucleus, and in this case, a scale bar represents 50 μm. b of FIG. 17 is a graph illustrating a calculation of a nuclear/cytoplasmic TAZ fluorescence ratio calculated from the immunofluorescent confocal image.
Figure 17:
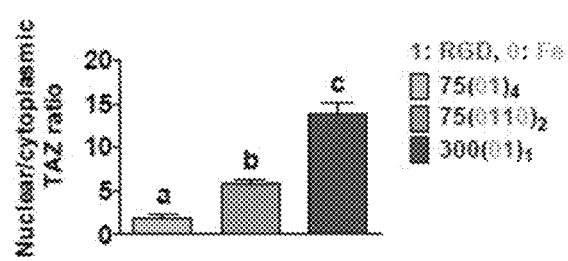

FIG. 17 is an immunofluorescent confocal image (a) of stem cells having actin polymerization inhibitor (cytochalasin D) cultured for 48 hours by using the nanobarcode according to the present invention against TAZ, vinculin, F-actin, and nucleus, and in this case, a scale bar represents 50 μm. b of FIG. 17 is a graph illustrating a calculation of a nuclear/cytoplasmic TAZ fluorescence ratio calculated from the confocal immunofluorescence image.

Figure 18:
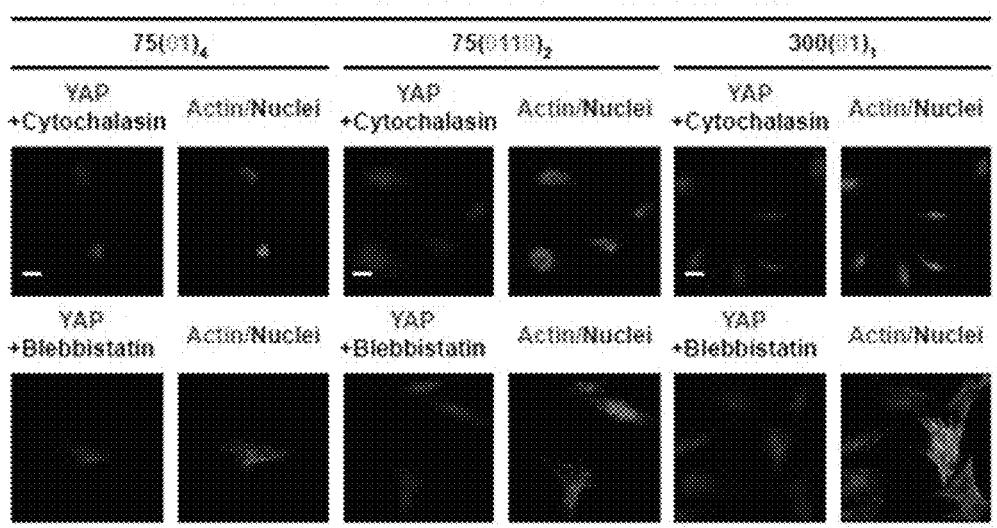
FIG. 18 is an immunofluorescent confocal image (a) of stem cells having actin polymerization inhibitor (cytochalasin D) and myosin II (blevisstatin) cultured for 48 hours by using the nanobarcode according to the exemplary embodiment of the present invention against YAP, F-actin, and nucleus, and in this case, a scale bar represents 50 μm. b of FIG. 18 is a graph illustrating a calculation of a nuclear/cytoplasmic YAP fluorescence ratio by inhibitors of Y27632, cytochalasin D, and blebbistatin calculated from the immunofluorescent confocal image.
Figure 18:
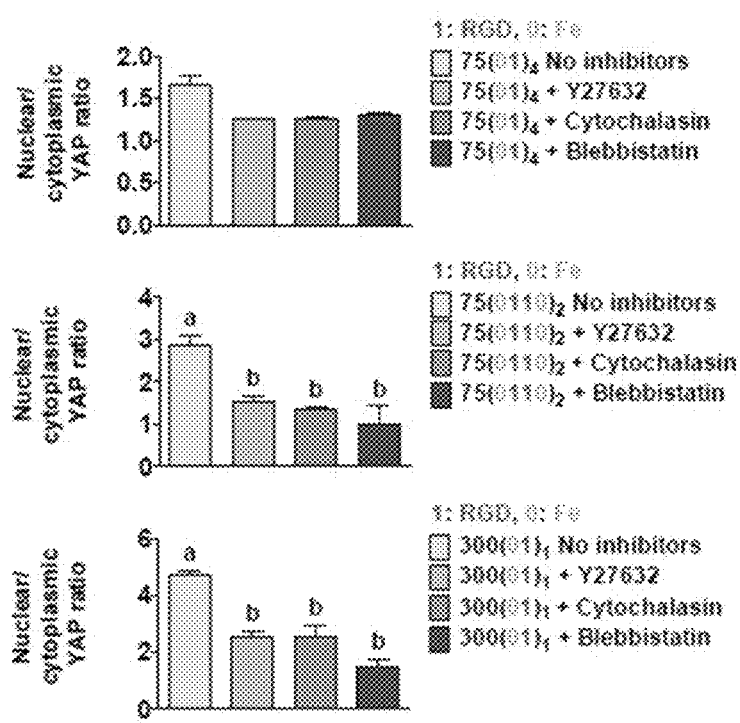

FIG. 18 is an immunofluorescent confocal image (a) of stem cells having actin polymerization inhibitor (cytochalasin D) and myosin II (blevisstatin) cultured for 48 hours by using the nanobarcode according to the present invention against YAP, F-actin, and nucleus, and in this case, a scale bar represents 50 μm. b of FIG. 18 is a graph illustrating a calculation of a nuclear/cytoplasmic YAP fluorescence ratio by inhibitors of Y27632, cytochalasin D, and blebbistatin calculated from the immunofluorescent confocal image.

Referring to FIGS. 17 and 18, in the nanobarcode with the highest nano-periodicity $[300(01)_1]$, vinculin expression and nuclear translocation of YAP were significantly reduced when actin polymerization, rho-associated protein kinase (ROCK), and myosin II were inhibited by cytochalasin D. Through this, it can be seen that the high nano-periodicity of the nanobarcode induces mechanotransduction-mediated differentiation of stem cells to facilitate focal adhesion assembly.

Experimental Example 5

Figure 19:
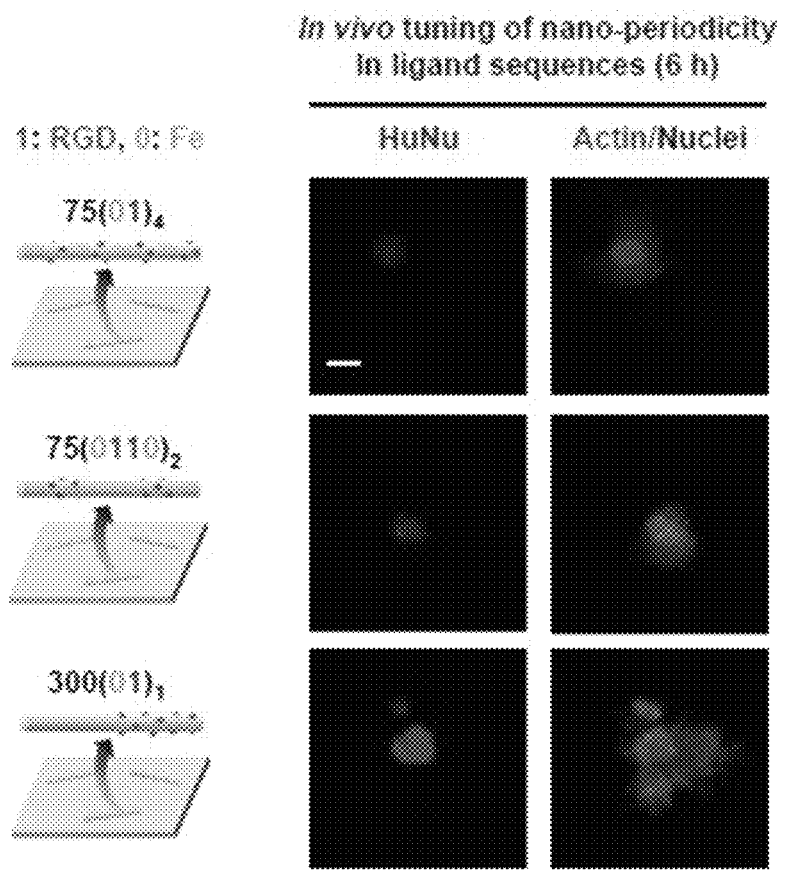
FIG. 19 is a diagram illustrating an experimental result for tuning adhesion of host stem cells in vivo by using the nanobarcode according to the exemplary embodiment of the present invention.
Figure 19:
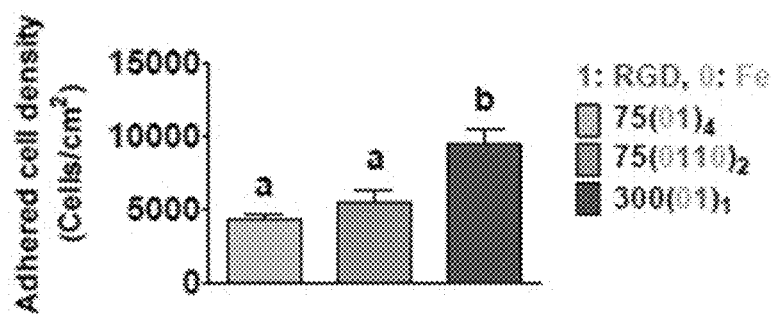
Figure 20:
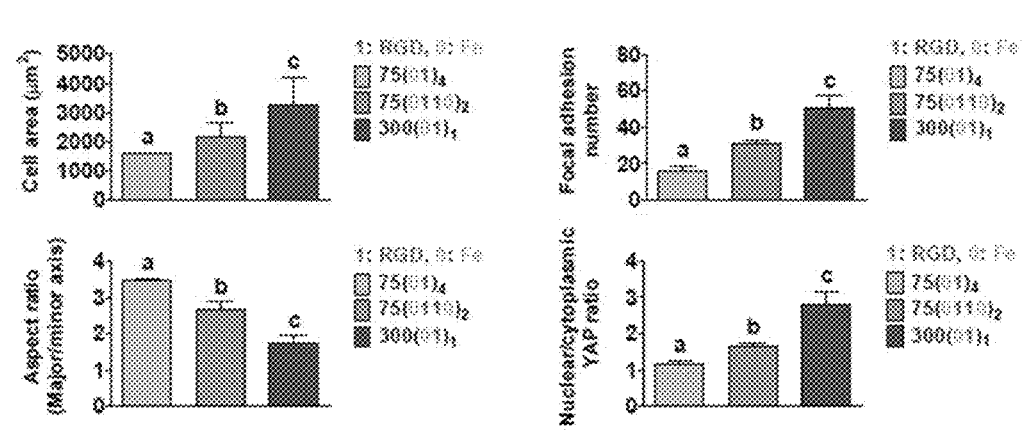
FIG. 20 is a diagram illustrating an experimental result for focal adhesion-mediated mechanotransduction of host stem cells in vivo by using the nanobarcode according to the exemplary embodiment of the present invention, and is a graph illustrating a calculation of a cell spread area, focal adhesion number, aspect ratio (major/minor axis ratio), and a nuclear/cytoplasmic YAP fluorescence ratio 6 hours after hMSC was injected on the subcutaneously implanted substrate from immunofluorescent confocal image illustrated in c of FIG. 12.

The experiment was performed to confirm the adhesion and mechanotransduction of stem cells in vivo by using the nanobarcode according to the present invention, and a result thereof is represented in FIGS. 19 and 20.

As illustrated in b of FIG. 12, the experiment was conducted by implanting the substrate including the nanobarcode under the skin of a nude mouse injected with hMSC.

FIG. 19 is a diagram illustrating an experimental result for tuning adhesion of host stem cells in vivo by using the nanobarcode according to the present invention. a of FIG. 19 is an immunofluorescent confocal image of stem cells against human-specific nuclear antigen (HuNu), F-actin, and nucleus in the case of including the nanobarcode with different nano-periodicities 6 hours after the injection of hMSC on the subcutaneously implanted substrate, and in this case, a scale bar is 20 μm. b of FIG. 19 is a graph of a calculation of density of adherent cells from the immunofluorescent confocal image. Referring to FIG. 19, immunofluorescence of human-specific nuclear antigen (HuNu) showed that hMSCs adhered onto the substrate in vivo by colocalization of HuNu and dapi-stained nuclei in the nanobarcodes of $[75(01)_4]$, $[75(0110)_2]$, and $[300(01)_1]$. The hMSCs adhered in considerably higher adherent cell density corresponding to increasing nano-periodicity presentation in ligand sequences. Furthermore, host immune cells were recruited and adhered onto the substrate in higher adherent cell density with increasing nano-periodicity in ligand sequences over a prolonged time following implantation.

FIG. 20 is a diagram illustrating an experimental result for focal adhesion-mediated mechanotransduction of host stem cells in vivo by using the nanobarcode according to the exemplary embodiment of the present invention, and is a graph illustrating a calculation of a cell spread area, focal adhesion number, aspect ratio (major/minor axis ratio), and a nuclear/cytoplasmic YAP fluorescence ratio 6 hours after hMSC was injected onto the subcutaneously implanted substrate from the immunofluorescent confocal image illustrated in c of FIG. 12.

Referring to c of FIG. 12 and FIG. 20, the immunofluorescent image showed that the high nano-periodicity in the ligand sequences in vivo facilitates focal adhesion, spread, and mechanotransduction of stem cells. This can be evidenced by the significantly large adherent cell spread area, focal adhesion number, vinculin expression in FA complexes, and nuclear translocation of YAP mechanotransduction. Through this, it is possible to effectively control focal adhesion and mechanosensing of stem cells under the condition in vitro or in vivo by tuning nano-periodicity in the ligand sequences.

What is claimed is:

1. A nanobarcode for controlling adhesion and differentiation of stem cells, the nanobarcode comprising:
    a nanobarcode in which a first segment including iron (Fe) and a second segment including gold (Au) are repeatedly formed; and
    an integrin ligand peptide bound to the second segment of the nanobarcode, wherein the integrin ligand peptide comprises a uniform distribution in a monolayer, and the nanobarcode comprises a density of 0.0235 to 0.0277 per square micrometer ($\mu m^2$), and the stem cells adhere to the second segment.

2. The nanobarcode of claim 1, wherein the nanobarcode is provided in a rod shape satisfying Equation 1 or Equation 2 below, $$[L(M_1M_2)q] \quad \text{[Equation 1]}$$

$$[L(M_1M_2M_2M_1)q] \quad \text{[Equation 2]}$$

herein, $M_1$ is the first segment, $M_2$ is the second segment, q is the number of times of the repetition of the first and second segments, and L is lengths of the first and second segments.

3. The nanobarcode of claim 2, wherein Equations 1 and 2 are any one of $[30(M_1M_2)_{10}]$, $[75(M_1M_2)_4]$, $[75(M_1M_2M_2M_1)_2]$, $[150(M_1M_2)_2]$, $[150(M_1M_2M_2M_1)_1]$, and $[300(M_1M_2)_1]$.

4. The nanobarcode of claim 1, wherein each of the first segment and the second segment is provided in a rod shape, and a length of the first segment is the same as a length of the second segment.

5. The nanobarcode of claim 1, wherein the first segment has a structure in which a carboxylate is substituted.

6. The nanobarcode of claim 1, wherein the nanobarcode has a rod shape having a circular cross section with a diameter of 50 nm to 100 nm and a length of 200 to 1,000 nm.

7. The nanobarcode of claim 1, wherein the integrin ligand peptide includes a thiolated integrin ligand peptide, and has a structure in which a thiol group of the integrin ligand peptide is chemically bound to the second segment.

* * * * *